United States Patent [19]
Damon

[11] Patent Number: 6,071,118
[45] Date of Patent: Jun. 6, 2000

[54] SELF-LIGATING ORTHODONTIC BRACKET

[75] Inventor: Dwight H. Damon, Spokane, Wash.

[73] Assignee: Damon Family Limited Partnership, Spokane, Wash.

[21] Appl. No.: 09/243,876

[22] Filed: Feb. 3, 1999

Related U.S. Application Data

[63] Continuation-in-part of application No. 09/024,931, Feb. 17, 1998, abandoned.

[51] Int. Cl.[7] ..................................................... A61C 3/00
[52] U.S. Cl. .................................................. 433/9; 433/10
[58] Field of Search ............................... 433/8, 9, 10, 11, 433/13, 14, 19, 24

[56] References Cited

U.S. PATENT DOCUMENTS

| | | | |
|---|---|---|---|
| 2,549,528 | 4/1951 | Russell | 433/13 |
| 2,671,964 | 3/1954 | Russell et al. | 433/13 |
| 3,131,474 | 5/1964 | Johnson | 433/14 |
| 3,772,787 | 11/1973 | Hanson | 433/14 |
| 4,023,274 | 5/1977 | Wallshein | 433/11 |
| 4,144,642 | 3/1979 | Wallshein | 433/11 |
| 4,248,588 | 2/1981 | Hanson | 433/11 |
| 4,386,909 | 6/1983 | Hanson | 433/20 |
| 4,712,999 | 12/1987 | Rosenberg | 433/8 |
| 4,927,360 | 5/1990 | Pospisil | 433/8 |
| 5,094,614 | 3/1992 | Wildman | 433/14 |
| 5,275,557 | 1/1994 | Damon | 433/10 |
| 5,322,435 | 6/1994 | Pletcher | 433/11 |
| 5,429,500 | 7/1995 | Damon | 433/10 |
| 5,439,378 | 8/1995 | Damon | 433/8 |
| 5,466,151 | 11/1995 | Damon | 433/10 |
| 5,474,446 | 12/1995 | Wildman et al. | 433/14 |
| 5,857,850 | 1/1999 | Voudouris | 433/11 |

FOREIGN PATENT DOCUMENTS

WO 97/42906  11/1997  WIPO .

OTHER PUBLICATIONS

A folded brochure titled Damon SL System—"Experience More Comfortable Orthodonic Treatment," bearing a 1997 copyright notice by "A" Company Orthodontics, Inc.

An instruction manual titled "Damon SL System—Straight–Wire Appliance," bearing a 1996 copyright notice by "A" Company Orthodontics, Inc.

A folder titled "Announcing a Radical Movement in Orthodontics—Finish–First," bearing a 1996 copyright by "A" Company Orthodontics, Inc.

A catalog sheet titled "Damon SL Archform" Cat. No. 0938420100. Rev. A published by "A" Company Orthodontics, Inc.

A patient handout titled "Congratulations!" bearing a 1996 copyright notice of "A" Company Orthodontics, Inc. Cat. (No. 0938420200A, indicating a printing date of May 1996.

An Internet publication printed on Jan. 21, 1998 at the following Worldwide Web address—http://members.home.net/str8tth/dmnweb2.htm; authored by William B. Hentosz, D.D.S.

(List continued on next page.)

*Primary Examiner*—John J. Wilson
*Attorney, Agent, or Firm*—Wells, St. John, Roberts, Gregory & Matkin, P.S.

[57] ABSTRACT

A self-ligating orthodontic bracket assembly includes a bracket including an transverse archwire slot. A first anterior surface of the bracket to one side of the slot terminates at one side slot surface. It is free of any anterior projections that would otherwise obscure viewing of the archwire slot opening by one installing or adjusting the bracket. A second anterior surface terminates at the remaining side slot surface. A ligating slide is guided within a pair of guides having inwardly facing guide slots located to the second side of the archwire slot. The ligating slide is movable between a retracted position and a cantilevered position over the archwire slot. The ligating slide is differentially colored with respect to the bracket. Various detents, both integral to the ligating slide or external to it and recessed within the bracket, are used to hold the ligating slide in its desired position relative to the supporting bracket structure.

53 Claims, 13 Drawing Sheets

OTHER PUBLICATIONS

An Internet publication (2 pages) printed on Jan. 21, 1998 from the Website for "A" Company Orthodontics, Inc. at the following Worldwide Web address—http://www.acortho.com/prods_damon.html; titled "Damon SL System."

An Internet publication printed on Jan. 21, 1998 at the following Worldwide Web address—http://www.globalserve.net/~tnplh/i-twins.html; titled "Five-Year Evaluation of Interactive Twin Mechanisms" and authored by Dr. John C. Voudouris, D.D.S., D. ORTH., M.SC.(D).

Voudouris, John C., DDS (Hons), Dorth, MSC, "Interactive edgewise mechanisms: Form and function comparison with conventional edgewise brackets," *American Journal of Orthodontics and Dentofacial Orthopedics,* vol. 111, No. 2, Feb., 1997: 119–140.

Voudouris, John C., Hon. DDS, DOrth, MSCD, "Seven Clinical Principles of Interactive Twin Mechanisms," JCO, Inc., vol. XXXI No. 1, Jan. 1997, 55–65.

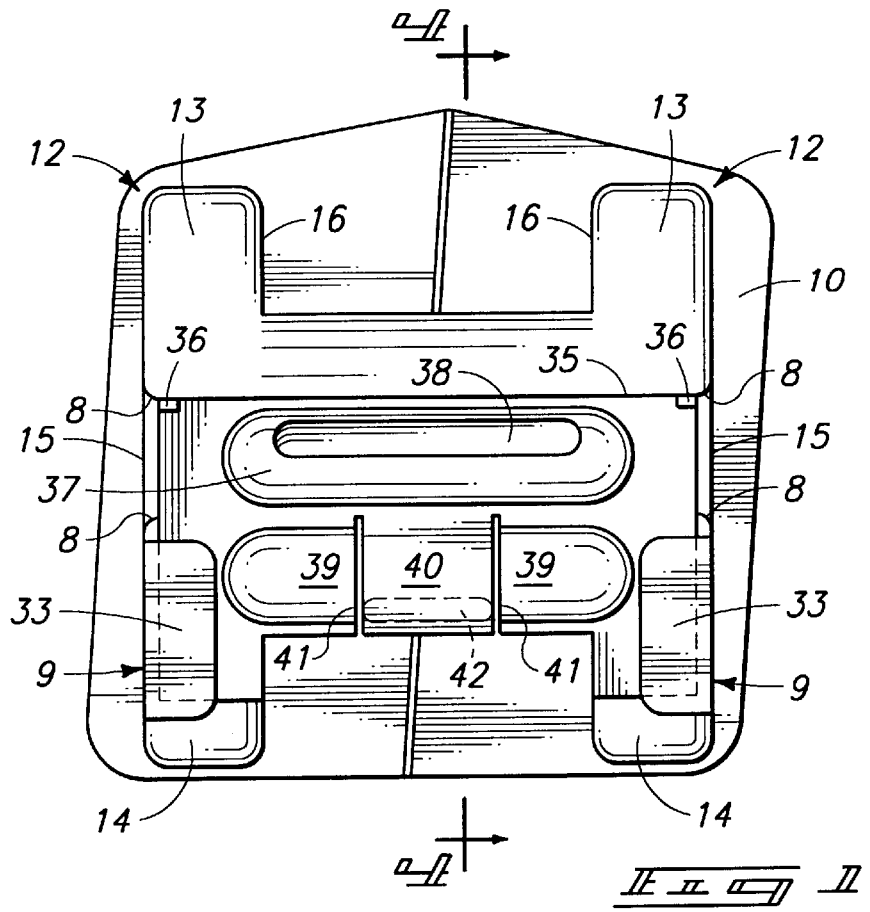
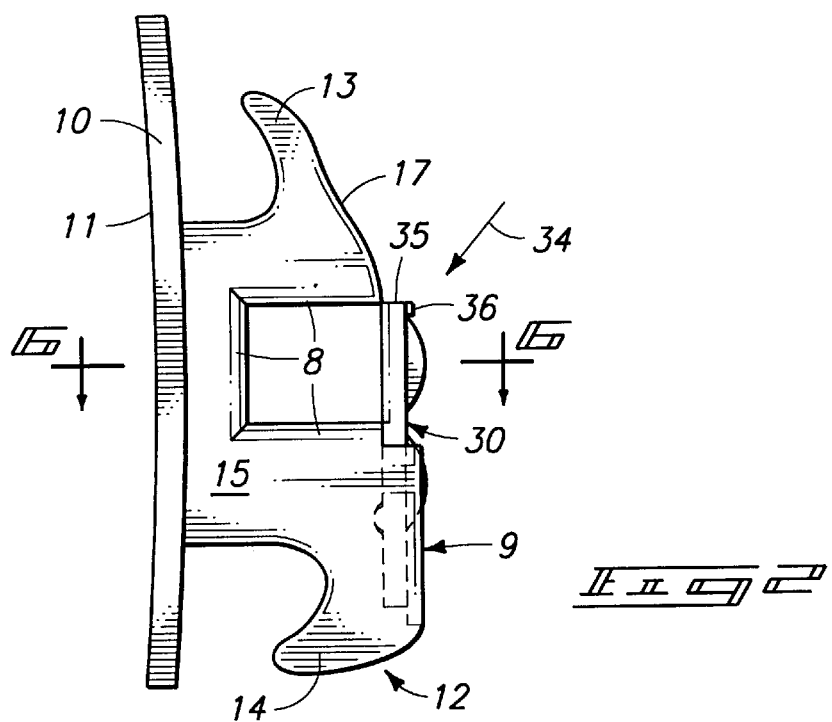

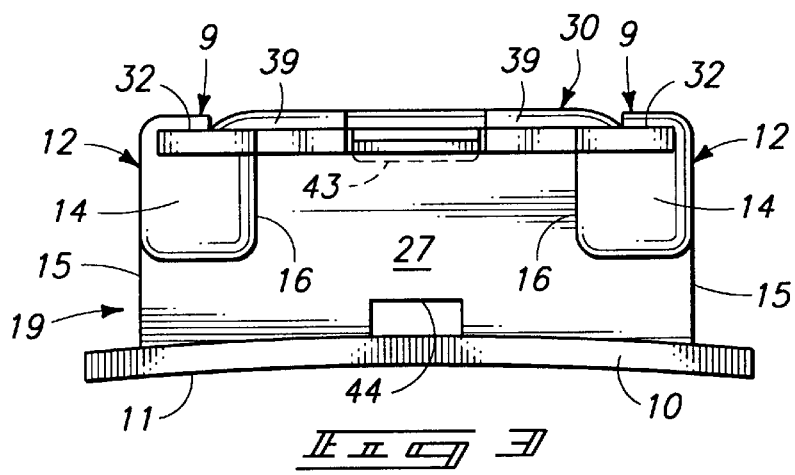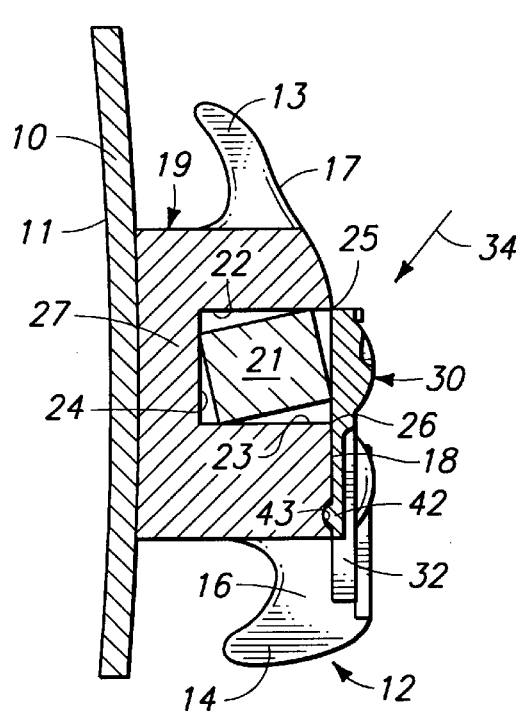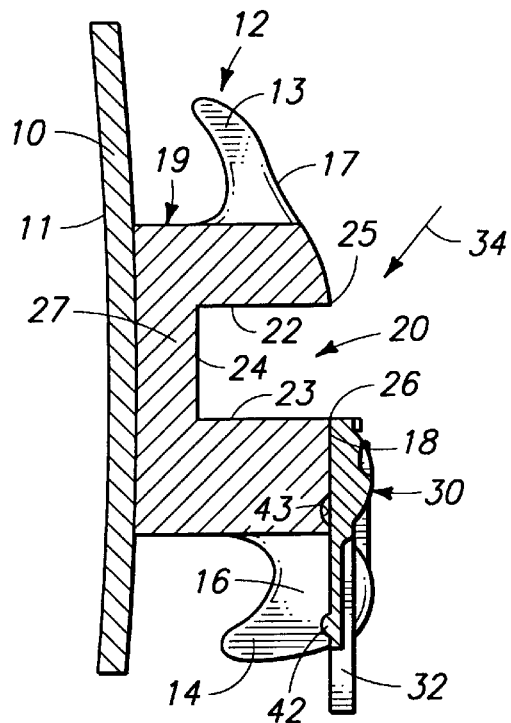

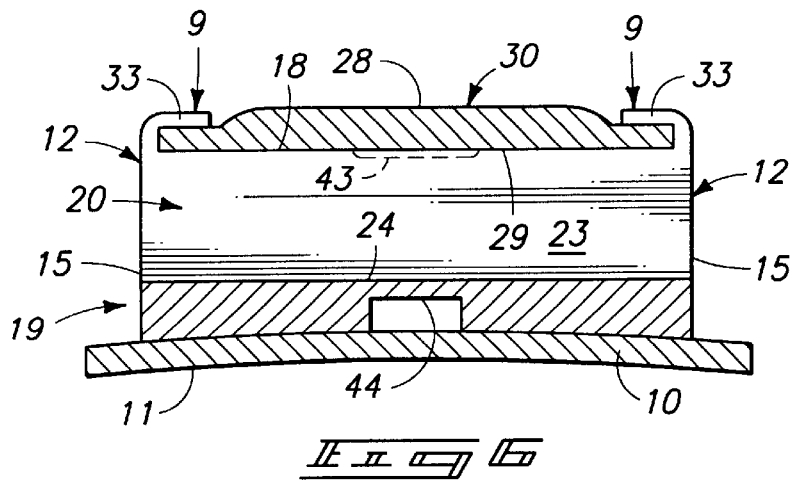
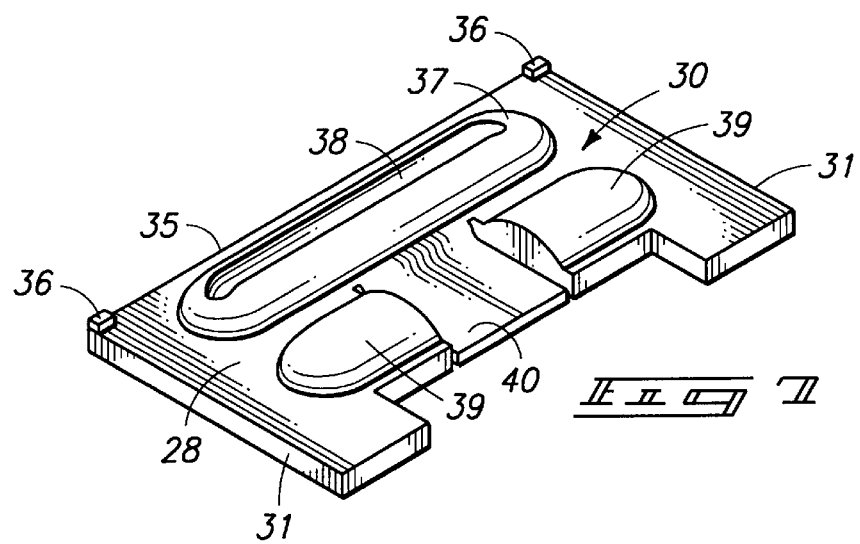
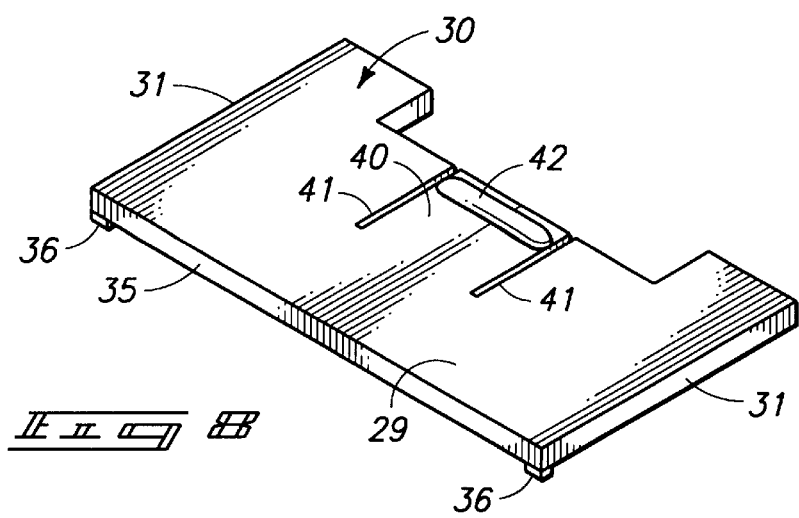

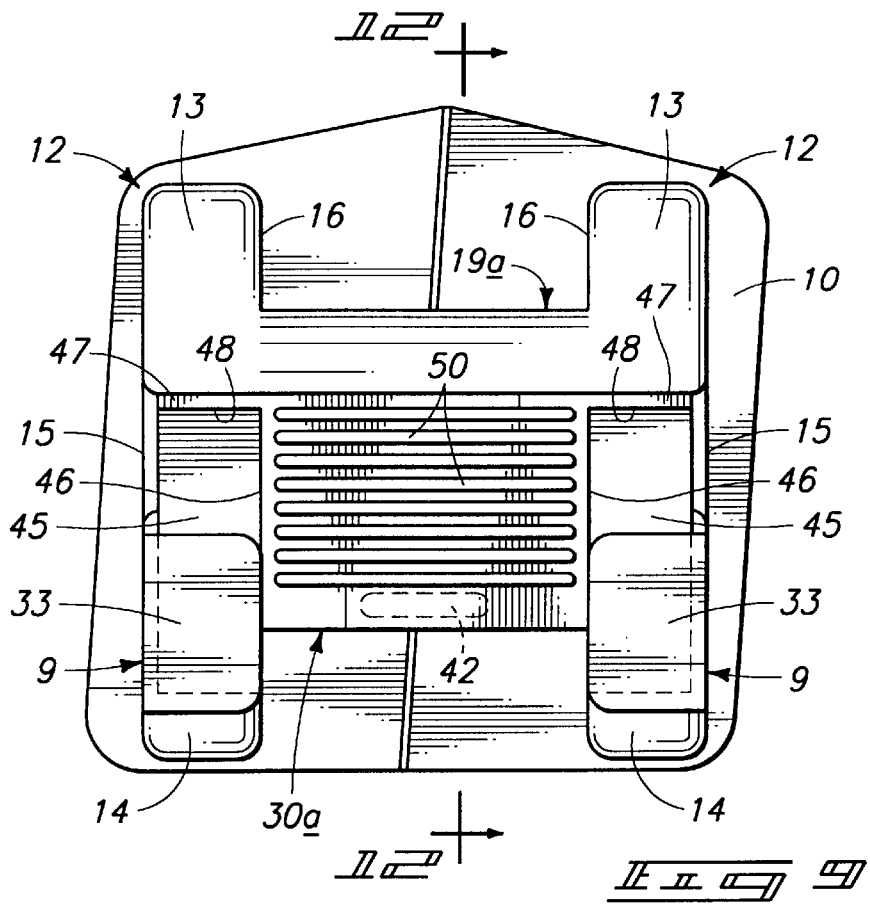
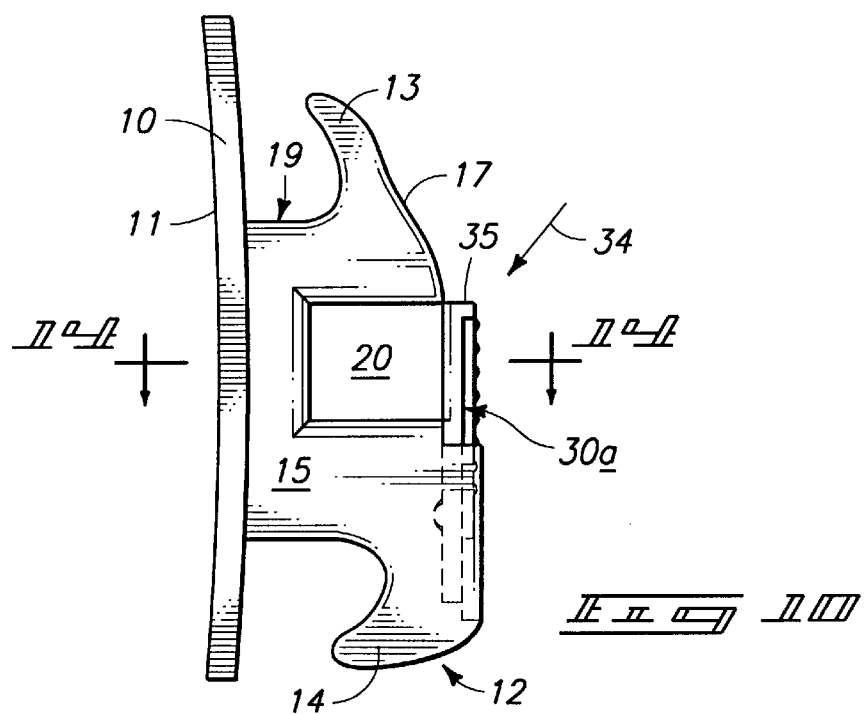

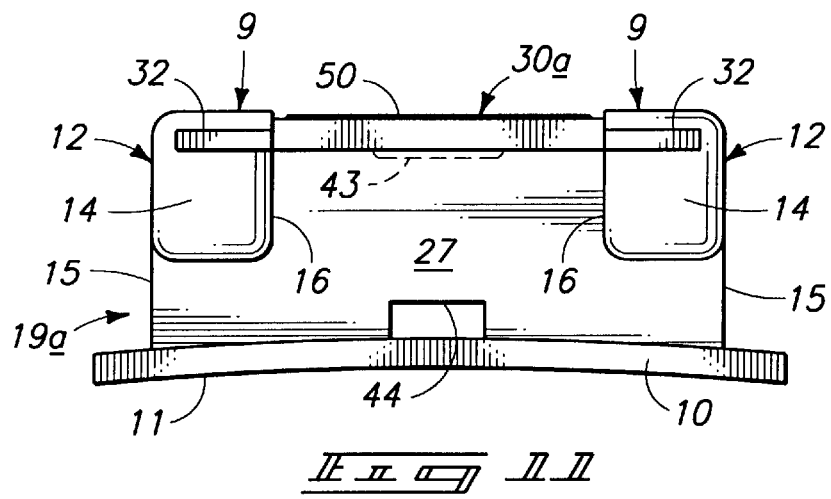
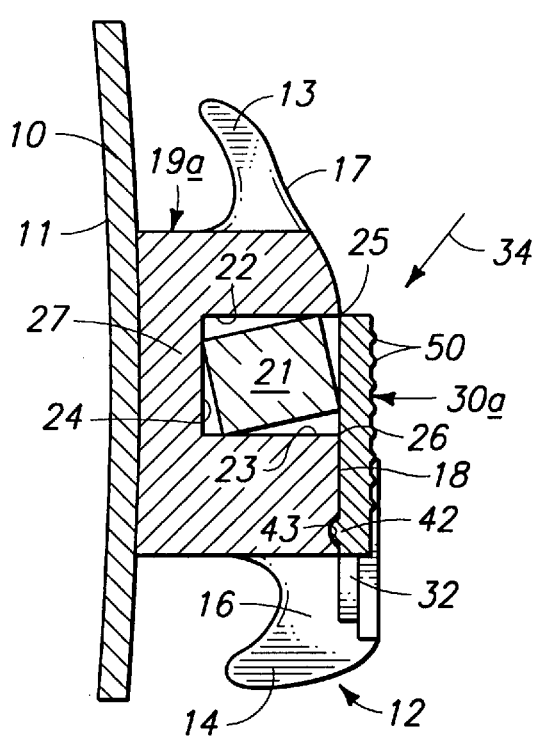
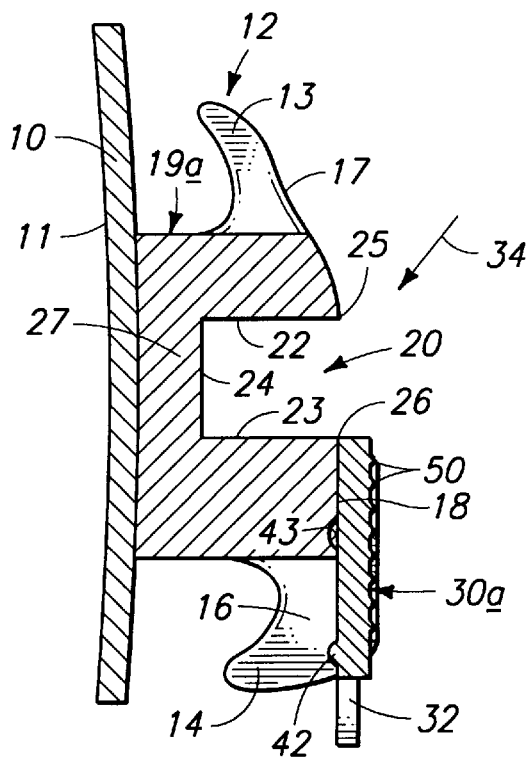

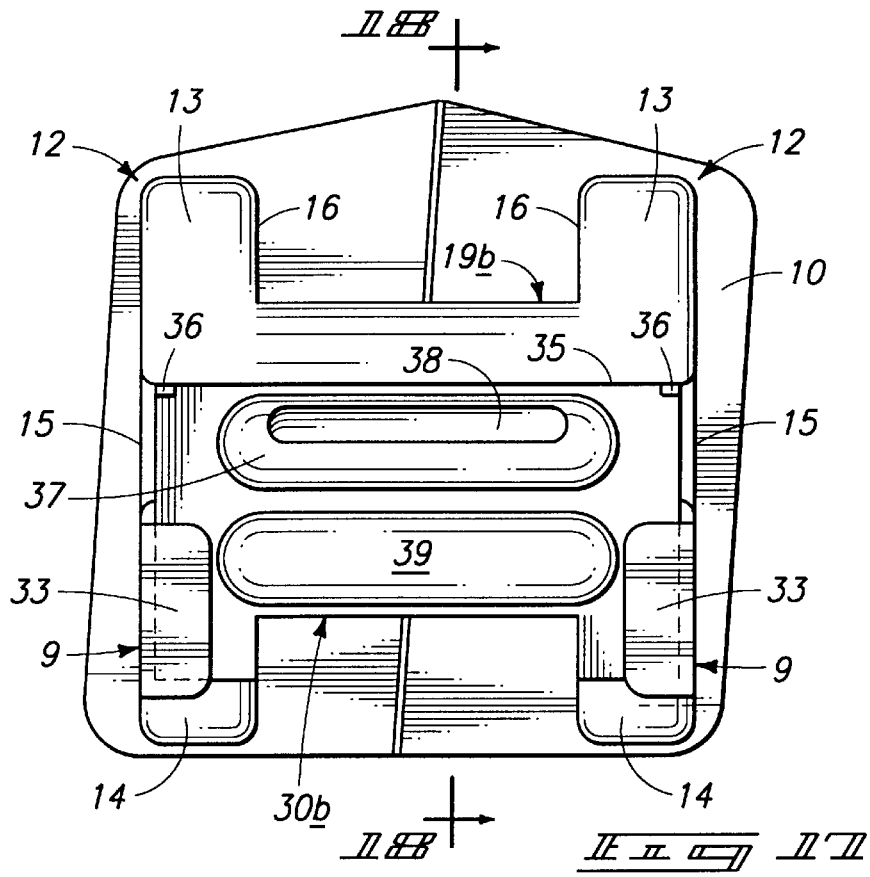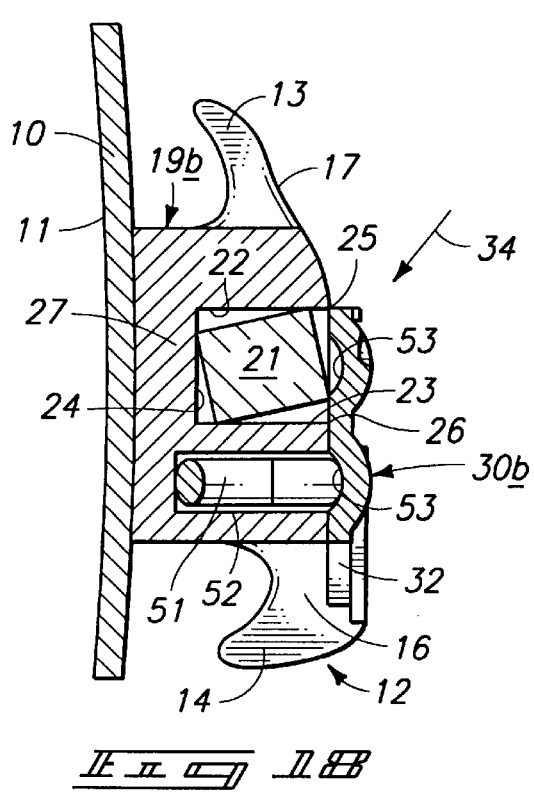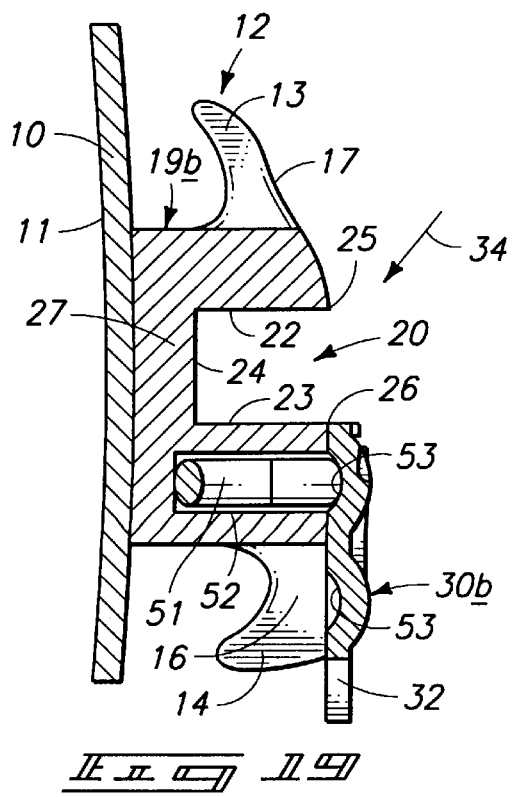

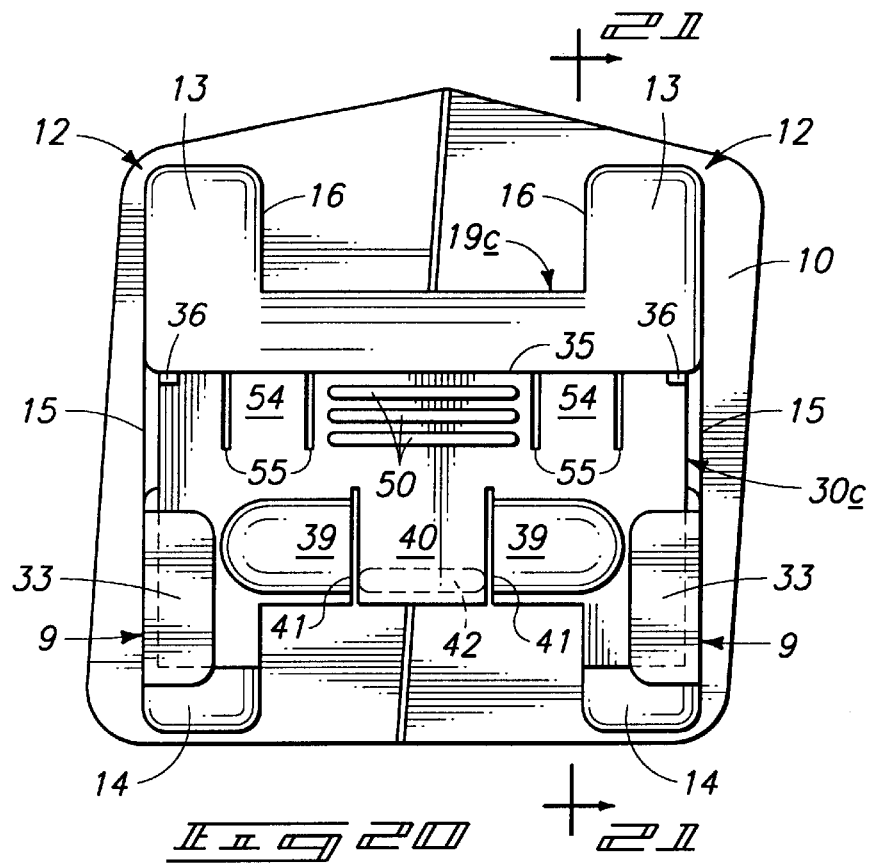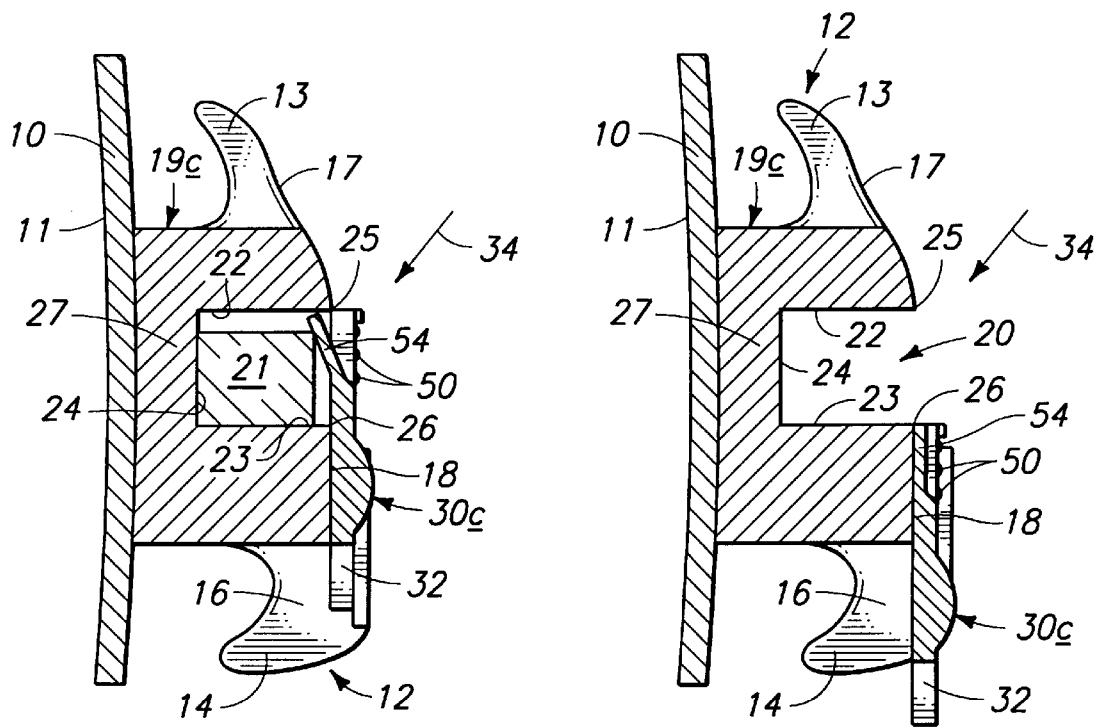
Fig 20
Fig 21
Fig 22

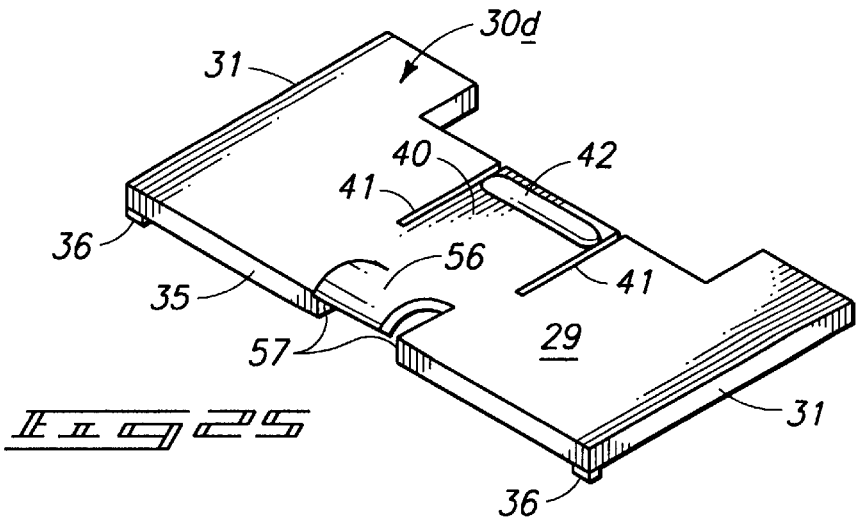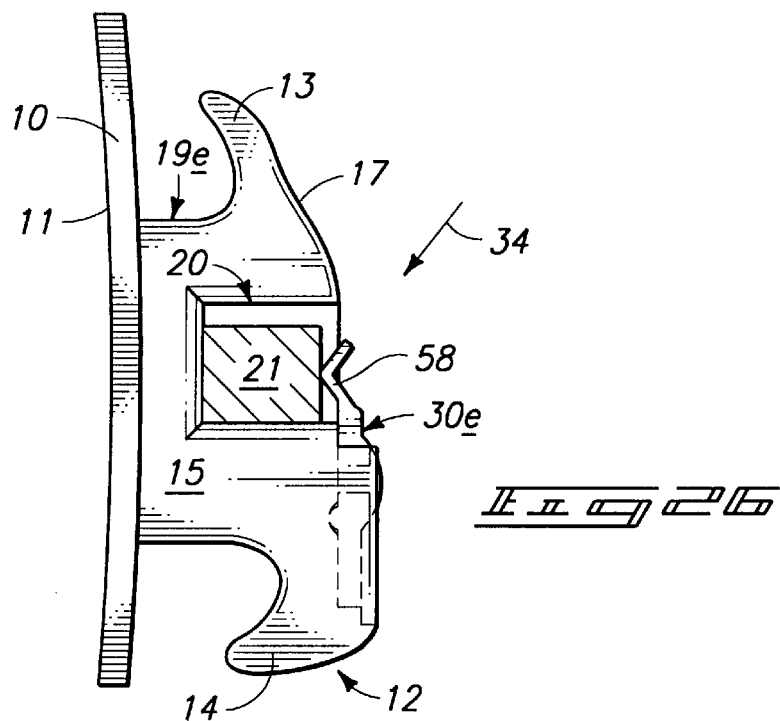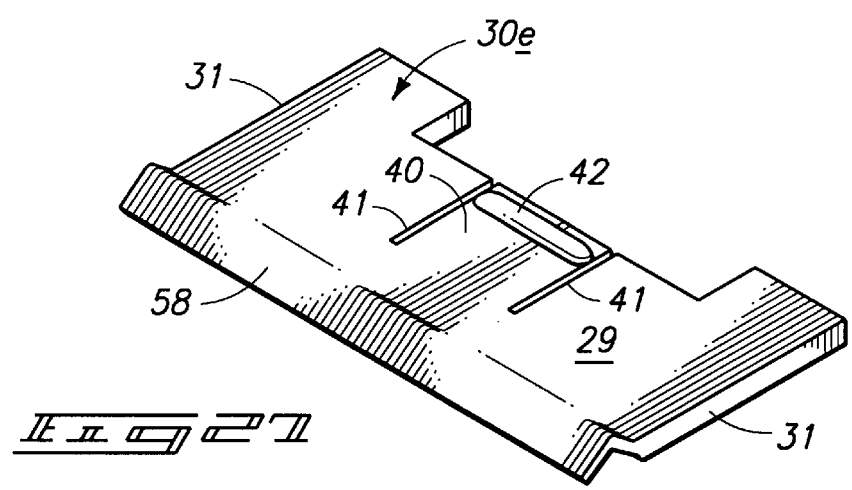

SELF-LIGATING ORTHODONTIC BRACKET

RELATED APPLICATION

This is a Continuation-in-Part of pending U.S. patent application Ser. No. 09/024,931, filed on Feb. 17, 1998, now abandoned and titled "Self-Ligating Orthodontic Bracket Assembly".

TECHNICAL FIELD

This disclosure pertains to self-ligating orthodontic brackets, and particularly to ligating slides designed for use with such appliances.

BACKGROUND OF THE INVENTION

Orthodontic brackets attached to teeth engage an archwire that exerts forces upon them to move the teeth. Such brackets typically include an archwire slot for reception of the archwire. An archwire slot can have any desired cross-sectional configuration or size to match the size and shape requirements of the archwire, or archwires, that are to be engaged within the slot.

Orthodontic brackets today are typically bonded to a tooth with the archwire slot oriented parallel to the occlusal plane. However, the slot can also be angularly oriented across the bracket when desired.

Most brackets in use today include cleat extensions referred to as tie wings or lugs. they project upwardly and downwardly in pairs at the top and bottom of the installed bracket, respectively. These extensions conventionally permit the archwire to be held within the archwire slot of the bracket by means of a twisted wire (ligature) or an elastomer O-ring.

Numerous attempts have been made to design brackets that are self-ligating. A detailed discussion of patents and publications describing various closures that have been proposed for the archwire slots of such orthodontic brackets can be found in U.S. Pat. No. 5,094,614 to Wildman, issued Mar. 10, 1992, which is hereby incorporated into this disclosure by reference.

The Wildman patent discloses a slidable closure that engages the front of the archwire. The closure is recessed from the front or anterior surfaces of the disclosed bracket. This is also true of sliding closures shown in U.S. Pat. No. 2,549,528 to Russell, which was issued on Apr. 17, 1951, U.S. Pat. No. 2,671,964 to Russell et al., which was issued on Mar. 16, 1954 and in U.S. Pat. No. 3,131,474, which was issued on May 5, 1964 to Johnson. The fact that such recessed sliding closures require the archwire also to be recessed within the archwire slot before the closure can be moved over the archwire makes it very difficult for the user to visually confirm that the archwire is properly seated within the archwire slot to facilitate closing of the slidable cover.

When using a conventional bracket and tying wires, proper seating of the archwire can be confirmed by visually noting that the anterior surface of the archwire is flush with the anterior surface of the bracket. It is desirable that a self-locking bracket provide similar visual reference capabilities to the user. This cannot be attained where no anterior surface of the bracket is available for visually referencing the position of an archwire within the archwire slot of the bracket.

A self-ligating bracket designed to mount an archwire flush with an anterior surface of an orthodontic bracket to facilitate visual positioning of the archwire during orthodontic treatment is shown in my earlier U.S. Pat. Nos. 5,275,557 (Jan. 4, 1994), 5,429,500 (Jul. 4, 1995) and 5,466,151 (Nov. 14, 1995). These patents are hereby incorporated into this disclosure by reference.

The bracket embodiments disclosed within my previous patent disclosures utilize a ligating slide or closure that is permanently retained on the bracket during use, whether the closure is left in an open or closed condition. This guards against accidental release of the closure while the bracket is worn on a tooth.

Most importantly, the closure was designed to leave the usual tying extensions that protrude from the top and bottom of the bracket fully accessible to other orthodontic attachments for the application of torsional forces to the teeth. The exposed tying lugs remain always available for repositioning of the bracket and tooth by use of tying wires or other conventional attachment systems. One achievement of this bracket is the provision of a ligating slide within a bracket that maintains the normal features of protruding tie wings or lugs required by the profession.

The bracket embodiments of my earlier patents also include a closure in the form of a ligating slide that can complete a continuous tube surrounding the archwire when the closure is in a closed position. This can be effectively achieved in a Siamese or twin bracket configuration without covering or interfering with projecting extensions on the bracket.

Another recent patent pertaining to a self-ligating orthodontic bracket is U.S. Pat. No. 5,322,435, issued to Pletcher on Jun. 21, 1994. The patent discloses a locking slide member that is flat and guided by upright slots formed along both sides of the bracket and spanning the archwire slot. A resilient member or detent is provided to retain the slide member in either the open or closed position. No tie wings or lugs are included in the illustrated bracket forms.

Miniaturization of orthodontic brackets is extremely important today in view of the development of modern high-technology archwires. Patients desire small brackets to reduce the visual impact of the brackets while they are being worn. Orthodontists desire smaller brackets in order to more effectively use the biasing forces available in the high technology archwires, it being recognized that the force applied to a bracket by the archwire is decreased with increasing bracket spacing between teeth.

One drawback to miniaturization of the brackets shown in my earlier patents is the fact that most of the embodiments wrap the cover over the sides of the bracket to engage grooves posterior to the archwire slot across the bracket. The thickness of the sliding cover therefore increases the total width of the bracket beyond that which is necessary due to the strength properties of the bracket itself. It is subject to tooth contact due to normal occlusion clearances in the mouth While the Pletcher U.S. patent does show a flat cover sliding within the lateral confines of a bracket, the guiding arrangement for the cover includes slots at both the superior and inferior sides of the archwire slot, thereby obscuring visual access to the critical corners of the archwire slots at the side edges of the bracket. Without this visual access being clear, one installing an archwire within a bracket cannot be certain as to proper seating of an archwire within the archwire slot before the slide cover is moved to a closed position.

BRIEF DESCRIPTION OF THE DRAWINGS

Preferred embodiments of the invention are described below with reference to the following accompanying drawings.

FIG. 1 is an elevational view of an assembled bracket with the cover shown in a closed position;

FIG. 2 is a side view of the bracket;

FIG. 3 is a bottom view of the bracket;

FIG. 4 is a sectional view as seen along line 4—4 in FIG. 1, also illustrating an archwire held within the bracket;

FIG. 5 is a view similar to FIG. 4, but showing the self-ligating slide in an opened position;

FIG. 6 is a sectional view taken along line 6—6 in FIG. 2;

FIG. 7 is a top perspective view of the self-ligating slide;

FIG. 8 is a bottom perspective view;

FIG. 9 is a view similar to FIG. 1, illustrating a second embodiment of the invention;

FIG. 10 is a side view of the bracket in FIG. 9;

FIG. 11 is a bottom view of the bracket shown in FIG. 9;

FIG. 12 is a sectional view taken along line 12—12 in FIG. 9;

FIG. 13 is a sectional view showing the open self-ligating slide;

FIG. 17 is a view similar to FIG. 1, illustrating a third embodiment of the invention;

FIG. 18 is a sectional view taken along line 18—18 in FIG. 17;

FIG. 19 is a sectional view showing the self-ligating slide in its open position;

FIG. 20 is a view similar to FIG. 1, showing a fourth embodiment of the invention;

FIG. 21 is a sectional view taken along line 21—21 in FIG. 20;

FIG. 22 is a sectional view showing the self-ligating slide in an open position;

FIG. 25 is a bottom perspective view of the self-ligating slide shown in FIG. 24;

FIG. 26 is a side view of a further form on a self-ligating slide;

FIG. 27 is a bottom perspective view of the self-ligating slide shown in FIG. 26;

DETAILED DESCRIPTION OF THE PREFERRED EMBODIMENTS

Figure 14:
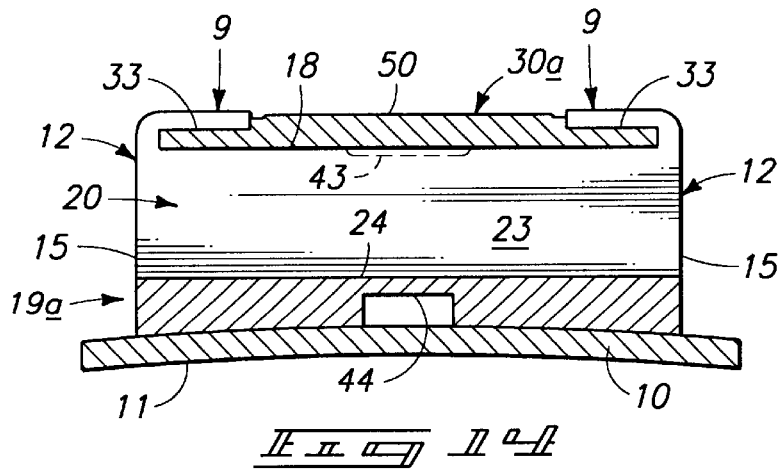
FIG. 14 is a sectional view taken along line 14—14 in FIG. 10.

This disclosure of the invention is submitted in furtherance of the constitutional purposes of the U.S. Patent Laws "to promote the progress of science and useful arts" (Article 1, Section 8).

Five illustrative forms of self-ligating orthodontic bracket assemblies are illustrated in the drawings. A first embodiment is shown in FIGS. 1–8. A second embodiment is shown in FIGS. 9–16, a third in FIGS. 17–19, and a fourth in FIGS. 20–23. Further variations in the features of self-ligating slides are disclosed in FIGS. 24–27. A fifth, and currently preferred embodiment is shown in FIGS. 28–32.

The illustrated details of the brackets and self-ligating slides can be used in many differing combinations within the scope of this disclosure. For this reason, the details of the illustrated orthodontic bracket assemblies are intended to be interpreted as being merely illustrative and are not to be taken as being restrictive of the practical combinations of such features within the scope of this disclosure and the appended claims.

When referring to the illustrated forms of the bracket assemblies, its front surfaces, directed outwardly from a supporting tooth, shall be referred to as anterior surfaces. Conversely, its rear surfaces, which face toward the tooth, shall be termed posterior surfaces. Directions along a bracket assembly generally parallel to the incisal or occlusal line shall be referred to as having width and being transverse. Conversely, perpendicular directions extending in generally upright orientations between the gingival line and the incisal or occlusal line shall be referred to as the height of the bracket assembly. The upright surfaces across the bracket assembly shall be termed its side surfaces and surfaces along the top and bottom of the bracket assembly shall be termed the incisal or occlusal surfaces or the gingival surfaces, respectively.

When referring to the directions of movement of the self-ligating slide relative to the bracket, the terms "inferior" and "superior" shall be used in an anatomical sense oriented in relation to a patient wearing the bracket. Thus, if a ligating slide is moved inferiorly, it will be moved in a downward direction. Conversely, if it is moved superiorly, it will be moved in an upward direction.

The incisal and occlusal surfaces, or the gingival surfaces, of the bracket are normally interrupted by extensions or lugs that form tie wings which serve as cleats or anchors for tying wires and other attachment devices. Such brackets are conventionally described as "Siamese brackets" or "twin brackets."

The configurations of the extensions included within the tie wings can take any desired conventional or unconventional form. The extensions at the top and bottom of the bracket can be located in different planes. The extensions at the top of the bracket can be located in a plane different from that of the extensions at the bottom of the bracket. The extensions might also have the same or different configurations at the superior end of the bracket than at its inferior end.

The archwire slots shown in the drawings are aligned transversely across each bracket in a direction parallel to the incisal or occlusal surfaces for general illustration purposes. However, the archwire slot across each bracket can be oriented at any desired angular configuration relative to its incisal or occlusal surfaces to effect a desired degree of tipping to a supporting tooth. In addition, the bracket can be oriented angularly relative to a supporting pad, thereby providing angular forces to the slot and engaged archwire when secured to a supporting tooth.

In order to properly fit upon the exterior surface of a selected tooth, the posterior surface across the pad of each bracket must be molded or otherwise formed to conform to the tooth with the archwire slot at the desired angular relationship to the archwire upon installation. Various placement angles can be provided on selected brackets by rotating the anterior surface contour across the pads of the brackets within a set. Alternatively, the archwire slots in a set of brackets can be arranged at selected angles by rotating the position of the protruding elements of each bracket relative to a pad having a properly contoured posterior surface. The archwire slot is then formed on the protruding portion of the bracket to match the amount of tipping to be imparted to a given tooth.

While the illustrated archwire slot is shown oriented perpendicular to the anterior surfaces of the bracket, it can be formed at any desired angle to the anterior surfaces, depending upon the desired torquing to which the supporting tooth is to be subjected.

The illustrated brackets are designed to be bonded directly to a tooth at either a facial or lingual tooth surface.

The present bracket can be made from any suitable material, including metals, plastics and ceramics, as well as a combination of such materials. The bracket and closure have generally been designed to be fabricated of metal, but the choice of materials is not critical to understanding or using this invention. The only limitation with regard to materials is the ability to efficiently fabricate or mold the bracket and ligating as mechanical structure capable of engagement by an archwire during orthodontic procedures.

The general concepts of the invention can best be understood from a study of the first embodiment of the assembled orthodontic bracket, illustrated in FIGS. 1–11. This form of the bracket includes a movable closure separately shown in FIGS. 7 and 8.

The illustrated bracket, identified generally by the numeral 19, includes a pad 10 having a posterior surface 11 adapted to be bonded directly to a tooth. Pad 10 can be constructed integrally with the bracket 19 or can be a separate component added to it during assembly.

The bracket 19 as shown in the drawings is a "Siamese" or twin bracket, having a pair of transversely spaced tie wings 12 located across the pad 10. Tie wings 12 project anteriorly from the bracket 19. Each tie wing 12 includes two opposed extensions 13 and 14 that project outwardly from bracket 19 between transversely spaced side surfaces.

While the bracket assemblies can be mounted on teeth in any desired orientation, it is preferable that the illustrated extensions 13 be superiorly positioned in both the upper and lower sets of brackets within the mouth of a patient, and that extensions 14 be inferiorly positioned. As will be evident below, this orientation provides maximum uninterrupted viewing of the entrance to the archwire slot of the bracket by a professional assisting a patient.

At a minimum, each tie wing 12 includes an outer side surface 15. In addition, the tie wing configurations shown in the drawings further include inwardly facing side surfaces 16.

The bracket 19 also includes first anterior surfaces 17 across the front of each first tie wing extension 13. The exposed anterior surfaces 17 extend across the full width of the bracket 19 and tie wing extensions 13. Similarly, the second tie wing extensions 14 also include second anterior surfaces 18.

The anterior surfaces 17 and are illustrated as being curved, while the anterior surfaces 18 are planar. They lead to opposite sides of a transverse archwire slot generally designated by the numeral 20. The archwire slot 20 spans the full width of the bracket 19, where it opens across the bracket side surfaces 15. The space along archwire slot 20 between the tie wings 12 can be open, but is preferably enclosed by bracket walls joining the tie wings. This provides a supporting enclosure for an archwire 21 across the full width of the bracket 19.

The archwire slot includes opposed and spaced side slot surfaces 22 and 23, plus an interconnecting anterior base 24. As can be seen in FIGS. 1 and 2, the intersections of the side slot surfaces 22,23 and anterior base 24 with the outer side surfaces 15 of bracket 19 are rounded or radiused, as indicated by reference numerals 8. This provides a smooth edge for engagement by an archwire located within the archwire slot 20 and eliminates high stress and pressure on the archwire surfaces in contact with the ends of the archwire slot. It further facilitates motion between the bracket and archwire as tooth movement occurs in the mouth of a patient.

Side slot surface 22 forms a first transverse anterior corner 25 with the archwire slot 20 where it intersects the anterior surface 17 of the first tie wing extensions 13. Side slot surface 23 similarly forms a second transverse anterior corner 26 with the archwire slot 20 where it intersects the anterior surface 18 of the second tie wing extensions 14.

It is important to note that the corner 25 is continuous or coextensive across the full width of bracket 19 between the side surfaces 15, which the corner 35 intersects. The anterior surface 17 across the first tie wing extension is free of any projections or closure guides projecting anteriorly beyond the corner 35. Thus, a clinician observing the installed bracket on a tooth has an unobstructed view of the open archwire slot 20 from its one side to guide him or her in proper bracket and archwire positioning procedures.

The slot surfaces 22, 23 and 24 are sized and configured in a manner complementary to the size and shape requirements of an archwire (or archwires) adapted to be received within the archwire slot. While the illustrated slot is rectangular and is designed specifically for reception of complementary rectangular archwires, it is to be understood that the slot can be configured as a cylinder or other cross-sectional shape in the manner presently known with respect to orthodontic bracket design. In use, the slot is partially or completely filled by the cross-sectional configuration of one or more archwires 21 located within it, as exemplified by the showing of FIG. 4.

In the illustrated form of the invention, the tie wings 12 are integrally joined within the structure of bracket 19. An intermediate wall section 27 extending across the tie wings 12 in the bracket 19 includes first and second wall sections transversely joining the twin upright tie wings at positions superior and inferior to the archwire slot 20, respectively. Each of the first and second walls includes a surface spaced from one another and flush with the previously-described side surfaces 22, 23 along the archwire slot. The intermediate wall section 27 further includes a surface flush with the previously-described base slot surfaces 24 to provide a continuous archwire slot across the full width of the illustrated bracket 19.

The intermediate wall section 27 serves as a structural boundary surrounding three sides of the archwire slot 20 in the space located between the tie wings 12. In combination with the closed ligating slide 30, it forms a continuous tube across the width of the bracket for reception and capture of an archwire.

It is to be understood that all or any selected portion of central bracket section 27 can be omitted if this is desired in a particular bracket assembly. This disclosure is intended to be inclusive of brackets having tie wings 12 which are free-standing and not interconnected other than through the supporting face 10, as well as brackets having a central bracket section provided at only one side of the archwire slot 20 or only across its base.

A closure complementary to the archwire slot is also provided on the illustrated bracket 19. It takes the form of a ligating slide 30 that is generally planar. The ligating slide movably engages the anterior surfaces 18 of the second tie wing extensions 14.

According to this disclosure, the ligating slide 30 is supported for motion relative to bracket 19 only along the second extensions 14 of the tie wings 12. The anterior portion of second extension 14 of each tie wing 12 includes a guide 9 having an upright inwardly facing guide slot 32. Each guide slot 32 is located anteriorly from the second anterior surfaces 18.

Ligating slide 30 an anterior surface 28 and a posterior surface 29 between opposed side edges 31. Slide 30 is slidably received only within the respective guide slots 32 of the two guides 9 formed along the second extensions 14. The ligating slide 30 is movably supported for being alternately positioned between a retracted first position (see FIG. 5) wherein it is clear of the archwire slot 20 and a cantilevered second position (FIGS. 1–4) projecting over the archwire slot from its support on the second extensions 14. For simplicity, the ligating slide 30 can be referred to as being "open" in its first position, and "closed" in its second position.

In the first embodiment of the invention, guide slots 32 are formed along the outer side surfaces 16 of the two second extensions 14 and along opposed inwardly projecting walls 33. The walls 33 at least partially overlap the width of each tie wing 12. The resulting guide slots 32 slidably receive the respective side edges 31 of ligating slide 30. The inner surfaces of walls 33 are parallel and spaced from the previously-described anterior surfaces 18 along the second extensions 14. They permit ligating slide 30 to be manually moved between the two positions illustrated in FIGS. 4 and 5.

The previously-described corners 25 and 26 across the opposed side slot surfaces 22 and 23 are parallel and located in a plane directly adjacent to the plane of the posterior surface 29 of ligating slide 30. Thus, when slide 30 is in its closed position (FIG. 4), the intersection formed between its posterior surface 29 and its open edge 35 is juxtaposed to the corner 25 of side slot surface 22. In this condition, the contiguous corners of the side slot surface 22 and slide 30 enclose the archwire slot 20 across the bracket.

When the ligating slide 30 is in its open position (FIG. 5), the intersection formed between its posterior surface 29 and its open edge 35 is juxtaposed to the corner 26 of side slot surface 23. In this condition, the contiguous corners of the side slot surface 23 and slide 30 provide uninterrupted access to the interior of archwire slot 20.

As can be seen in FIGS. 2, 4 and 5, the cantilevered support for the ligating slide 30 assures a user of an unobstructed oblique view of the archwire slot 20 when looking toward the mouth of one wearing the brackets, as illustrated by arrow 34. This is true whether the bracket is mounted on a lower tooth or an upper tooth. A clinician can therefore readily observe the position of an archwire 21 relative to the boundaries of the archwire slot 20 before closing the ligating slide 30. To assure full width visual and physical access to the archwire slot 20, the open edge 35 of the ligating slide 30 is preferably flush with the inferior side slot surface 23 when the ligating slide 30 is in its retracted or open position (FIG. 5).

The anterior surface of ligating slide 30 has a pair of protruding stops 36 at its sides and adjacent to its open edge 35. Stops 36 are designed to abut the ends of walls 33 so as to limit the opening movement of the ligating slide 30 relative to the bracket 19.

Ligating slide 30 is essentially planar and rigid. However, it is desirable to reinforce its strength by the addition of one or more transverse enlarged ribs 37.

As shown in FIGS. 1 and 7, the ligating slide 30 might include a full width rib 37 adjacent to its open edge 35 and a second interrupted rib 39 parallel to it. The overall lengths of the ribs 37, 39 should be such that they extend laterally to locations directly adjacent to the inwardly facing upright edges of walls 33. Ribs 37, 39 should lightly rub along walls 33 to assist in maintaining the ligating slide in an upright orientation and to further guide it while moving relative to the bracket 19.

The full length rib 37 further includes an exterior transverse groove 38. The groove 38 can be dimensioned and shaped to be engaged by a manipulating tool (not shown) designed to assist in opening and/or closing of the ligating slide when it is in use.

A further advantage of the ribs 37 is that they interrupt the plane outer surface of ligating slide 30, and thereby minimize the "mirror" effect of the slide surface when viewed within the mouth of a person undergoing orthodontic treatment.

It is preferable to include a detent mechanism in the bracket assembly so as to positively position the ligating slide 30 in its alternate positions, as shown in FIGS. 4 and 5. In general, this involves provision of a detent and a complementary recess operably engageable between a posterior surface of the ligating slide 30 and the bracket 19 for fixing the position of the ligating slide relative to the bracket when the ligating slide is in its cantilevered second position.

In this first form of the ligating slide 30, the detent is formed on a central tab 40, separated from the remainder of the ligating slide by parallel slots 41 formed through it.

The thickness of tab 40 is shown as being less than the thickness of the remainder of the ligating slide 30. At its underside it includes a protruding transverse rib 42 adapted to be received in a complementary groove 43 formed at the anterior surface 18 extending across the bracket 19. The relatively thin nature of tab 40 provides a spring support for the rib 42, and flexes sufficiently to permit the rib 42 to enter and exit groove 43 in response to movement of ligating slide 30. This form of detent further permits fine adjustment of the detent force by a user, who can bend the tab 40 in either direction when it is overhanging the bracket 19 with the ligating slide 30 in its retracted or open position (FIG. 5).

The bracket 19 shown in FIGS. 1–6 further includes an upright open rectangular slot 44 for reception of auxiliary orthodontic devices, such as posts or anchors for applying selected forces to adjacent brackets or to the archwire itself.

The embodiments of the bracket assembly as illustrated in FIGS. 9–23 are basically similar to that described with respect to FIGS. 1–8. Identical reference numerals are used in these figures, as well as in FIGS. 24–27, for previously-described elements common to the preferred embodiment detailed above. The following discussions will be directed only to those features modified or added within the additional embodiments.

A second embodiment of the bracket assembly is detailed in FIGS. 9–16. In this form of the bracket assembly, the walls 33 forming guide slots 32 overlap the full width of the respective tie wings 12 in a modified bracket 19a. In addition, the thickness of guide slots 32 is reduced, and the side edges of ligating slide 30a are correspondingly reduced in thickness about the area shown at 45. The inner boundaries of areas 45 are defined by upright shoulders 46 which bear against the inner edges 47 along the widened walls 33.

The slidably interfitting guide slots 32 and reduced thickness areas 45 provide substantial bearing surfaces for structurally and slidably supporting the ligating slide 30a on the bracket 19a. Transverse shoulders 48 adjacent the open edge of the ligating slide 30a provide physical stops to limit opening movement of the ligating slide 30a when they abut against the walls 33.

Figure 15:
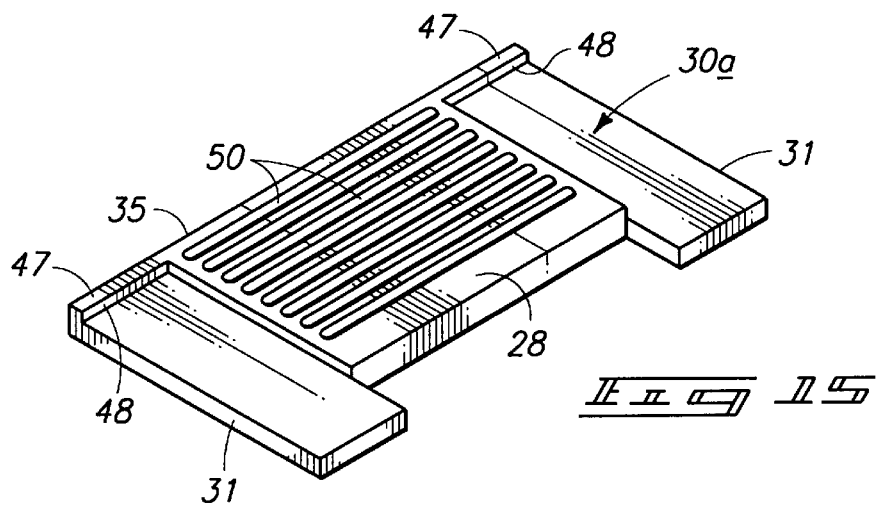
FIG. 15 is a top perspective view of the self-ligating slide shown in FIG. 9.
Figure 16:
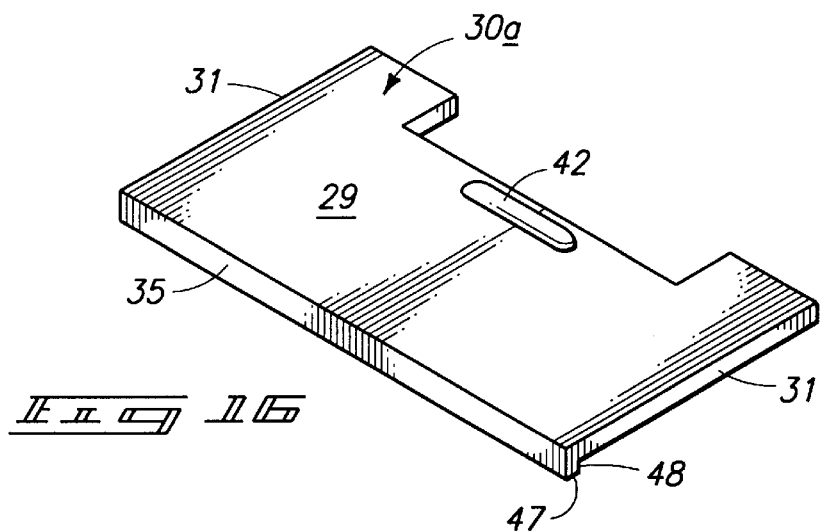
FIG. 16 is a bottom perspective view.
Figure 23:
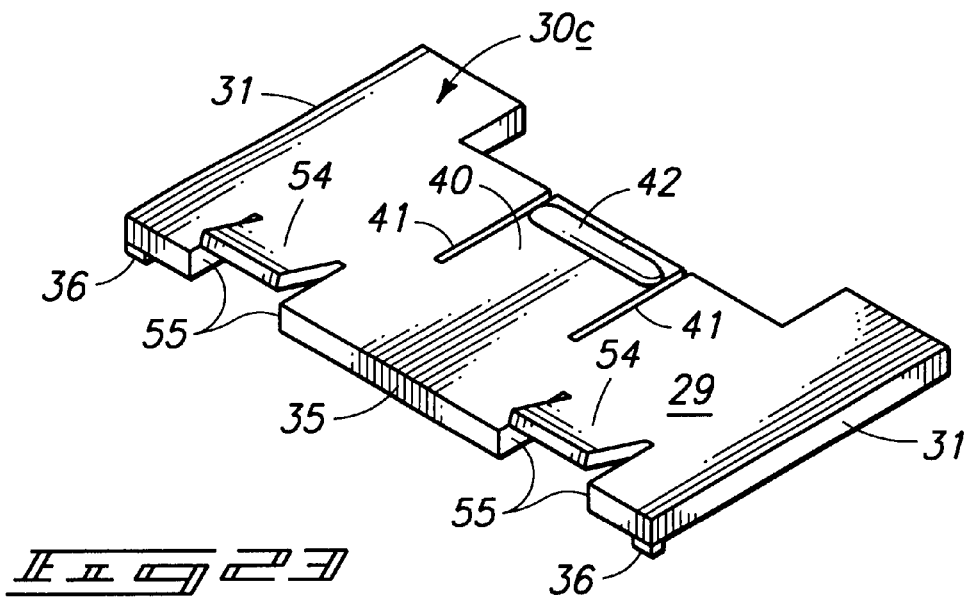
FIG. 23 is a bottom perspective view of the self-ligating slide shown in FIG. 20.

As can be seen in FIGS. 9 and 15, a series of small elongated transverse ribs 50 are formed across the outer surface of the ligating slide 30a. Their purpose is to interrupt the planar surface area, thereby minimizing the reflective properties of the ligating slide 30a. If desired, grooves can be used in place of the illustrated ribs 50.

In this form of the invention, the rib 42, which serves as a detent in combination with a complementary groove 43 on the bracket 19a, is formed integrally within the structure of the ligating slide 30a. The thickness of the ligating slide 30a is such as to provide sufficient flexibility to enable the rib 42 to enter and exit groove 43 in response to sliding movement of the ligating slide 30a. This action is indicated in the sectional views at FIGS. 12 and 13.

In general, the operation of the bracket assembly shown in FIGS. 9–16 is substantially similar to that described with respect to FIGS. 1–8.

The embodiment of the bracket assembly illustrated in FIGS. 17–19 is designed to utilize a recessed spring-biased detent system generally disclosed in my prior U.S. Pat. No. 5,466,151, which has been incorporated by reference into this disclosure. As detailed in the referenced patent, a bent flat spring 51 is fitted within a recess 52 at the central section 27 of the bracket 19b. The ligating slide 30b overlies spring 51 and is provided with two transverse grooves 53 across its underside, the grooves 53 being adapted to receive a protruding portion of the flat spring 51. Spring 51 deflects within the bracket 19b to permit the ligating slide 30b to be shifted between its extended position (FIG. 18) and its retracted position (FIG. 19). In all other respects, this form of the bracket assembly is identical to that detailed in FIGS. 1–8.

FIGS. 1–20 describe "passive" forms of the ligating slides, which minimize friction against the archwire within an archwire slot by merely serving as a closure across the archwire slot opening. FIGS. 21–27 pertain to variations in the ligating slide, designed to accommodate users desiring features of an "active" ligating slide, which applies a yieldable force against an archwire captured across an orthodontic appliance.

In the modified forms of the ligating slide shown in FIGS. 21–27, an integral leaf spring bent is inwardly along its transverse open edge. This gives the manufacturer and the user choices between a purely "passive" ligating slide, as described in the previous embodiments of the self-ligating orthodontic bracket assemblies, a combination "active/passive" ligating slide, as described with respect to FIGS. 20–25, and a purely "active" ligating slide, as described with respect to FIGS. 26 and 27. Since the ligating slides of this disclosure are readily disassembled and reassembled, the active or passive nature of their open edges can be modified at any time by simply substituting a new ligating slide having the desired spring pressure characteristics or eliminating such characteristics entirely.

In some instances, active or active/passive ligating slides might be desirable during earlier phases of orthodontic treatment, when lighter and smaller archwires are typically utilized. Passive ligating slides can be used as closures for common supporting brackets on teeth when using heavier and larger archwires during later phases of treatment.

The embodiment of the bracket assembly shown in FIGS. 20–23 illustrates inclusion of a combination active/passive ligating slide 30c. The ligating slide 30c has an open transverse edge comprising alternate rigid areas and bent tabs 54 which serve as leaf spring areas. The ligating slide 30c can have one or more bendable tabs 54 defined across its open edge 35. In the illustrated example there are two tabs 54 bounded by slots 55 formed through the ligating slide 30c. Tabs 54 have a reduced thickness to facilitate bending of them from the plane of the remainder of the ligating slide 30c.

Tabs 54 are bent toward the base of archwire slot 20 to serve as biasing leaf springs that exert a yieldable force on the archwire 21 when the ligating slide 30c is in its cantilevered extended position (see FIG. 21). The amount of bend provided along the interconnection between the rigid portion of ligating slide 30c and the tabs 54 can be manually adjusted by a user as required during treatment of a patient.

When the ligating slide 30c is retracted to its open position, the yieldable tabs 54 will move anteriorly in response to engagement of the anterior surfaces of the bracket 19c (FIG. 22). If desired, clearance recesses (not shown) can be provided at the anterior of the bracket 19c to receive tabs 54 without such bending action.

In this version of the bracket assembly, the outer surface of the ligating slide 30c includes an interrupted rib 39 and tab 40, as detailed above with respect to FIGS. 1–8. In addition, parallel small ribs 50 are provided between the bendable tabs 54, in a manner similar to the ribs illustrated in FIGS. 9–16.

Figure 24:
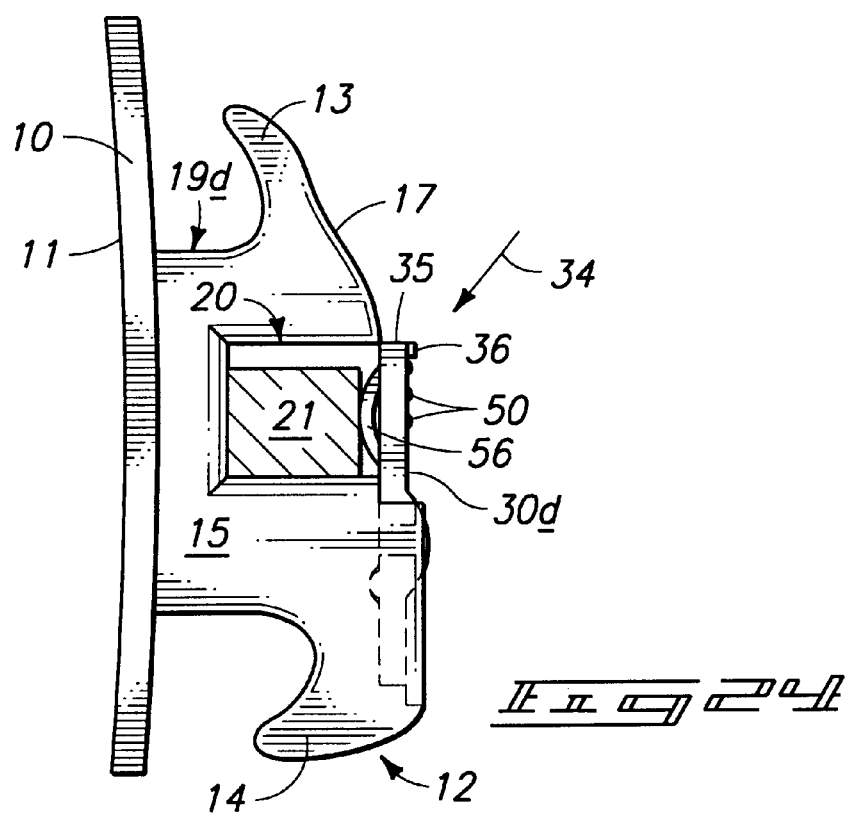
FIG. 24 is a side view of an alternate form on a self-ligating slide.
Figure 28:
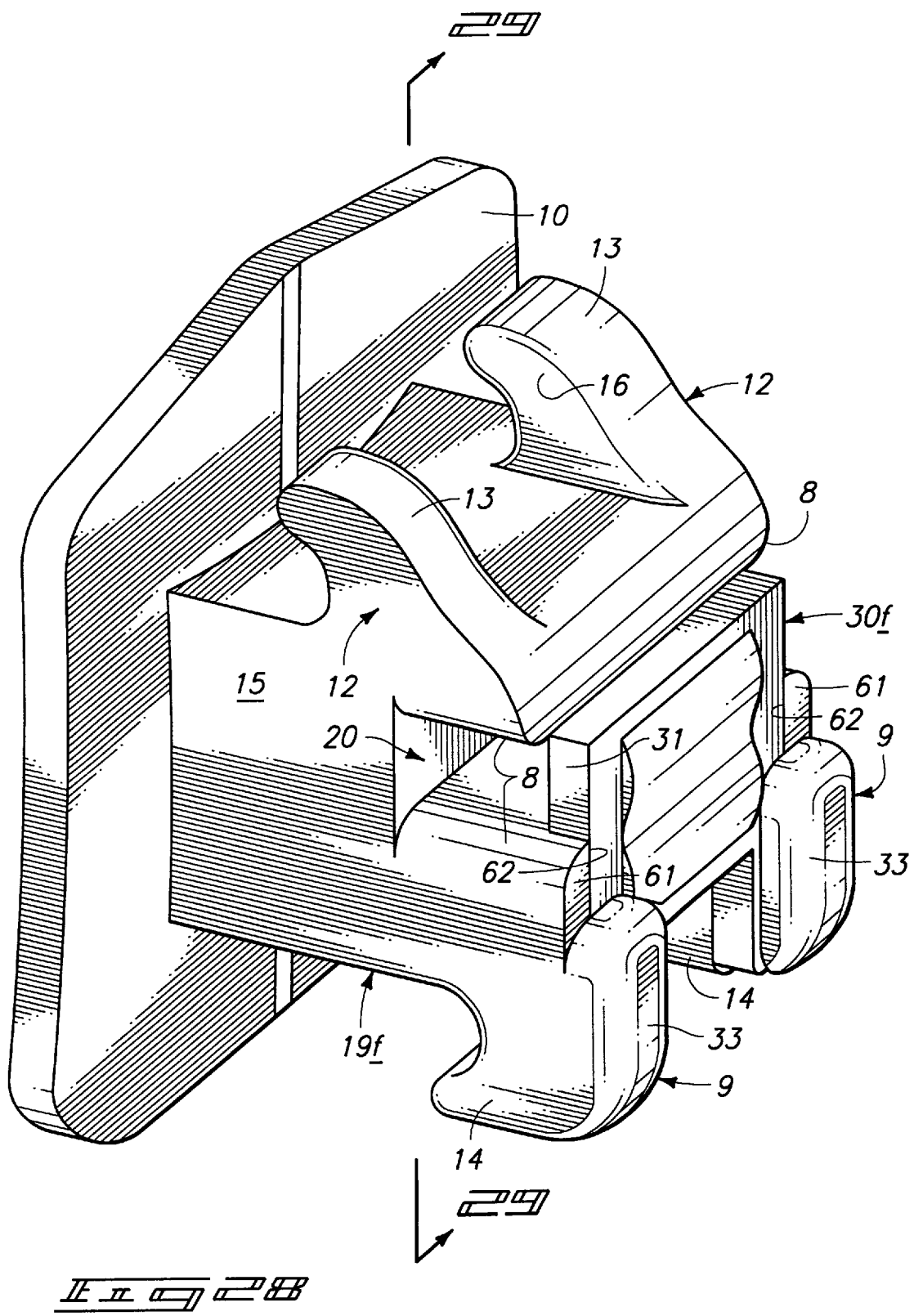
FIG. 28 is a perspective view of a currently-preferred form of the self-ligating bracket assembly.

FIGS. 24 and 25 show a further variation of an active/passive ligating slide 30d. It can be utilized in conjunction with the features of any one of the brackets previously described. The open transverse edge of the ligating slide 30d constitutes an active/passive closure over the archwire slot when the ligating slide is in its cantilevered second position (see FIG. 24). It includes a single tab 56, formed between slots 57 in the rigid ligating slide 30d.

Tab 56 has an arcuate configuration to facilitate sliding engagement over an archwire 21 formed across a bracket 19d (see FIG. 24) and to locate the point of leaf spring pressure on the archwire 21 at a mid-position across the archwire slot 20.

An additional variation of the ligating slide 30e is shown in FIGS. 26 and 27. In this form, the ligating slide 30e is an active slide that can be utilized in conjunction with the features of any one of the brackets previously described when only active spring pressure on an archwire is desired by a user. A bent tab 58 extends across the full width of the ligating slide 30e. In this form, the ligating slide 30e has only one central bent tab 58. Ligating slide 30e has an open transverse edge comprising a continuous leaf spring area.

The open transverse edge of the ligating slide 30e constitutes an active closure over the archwire slot when the ligating slide is in its cantilevered second position. It might be constructed of a thin cross section of the material used in the formation of the rigid ligating slide 30e. It is shown with transverse angular bends to concentrate the leaf spring forces near the mid-point across an archwire slot 20 within a supporting bracket 19e (see FIG. 26).

A currently-preferred version of the bracket assembly is shown in FIGS. 28–32. It has been modified to provide greater compatibility of the bracket with the normal occlusion of the teeth found within the mouths of patients and to also provide minimal interference due to contact with overlapping lips tissue. By minimizing the overall thickness of the bracket at its superior side, the bracket will normally avoid opposing tooth contact resulting from occlusion of the upper teeth over the lower teeth. In addition, by minimizing the thickness of the bracket, the engagement of the bracket by the inner surfaces of the lips will be minimized when the bracket is placed on an upper tooth.

Figure 29:
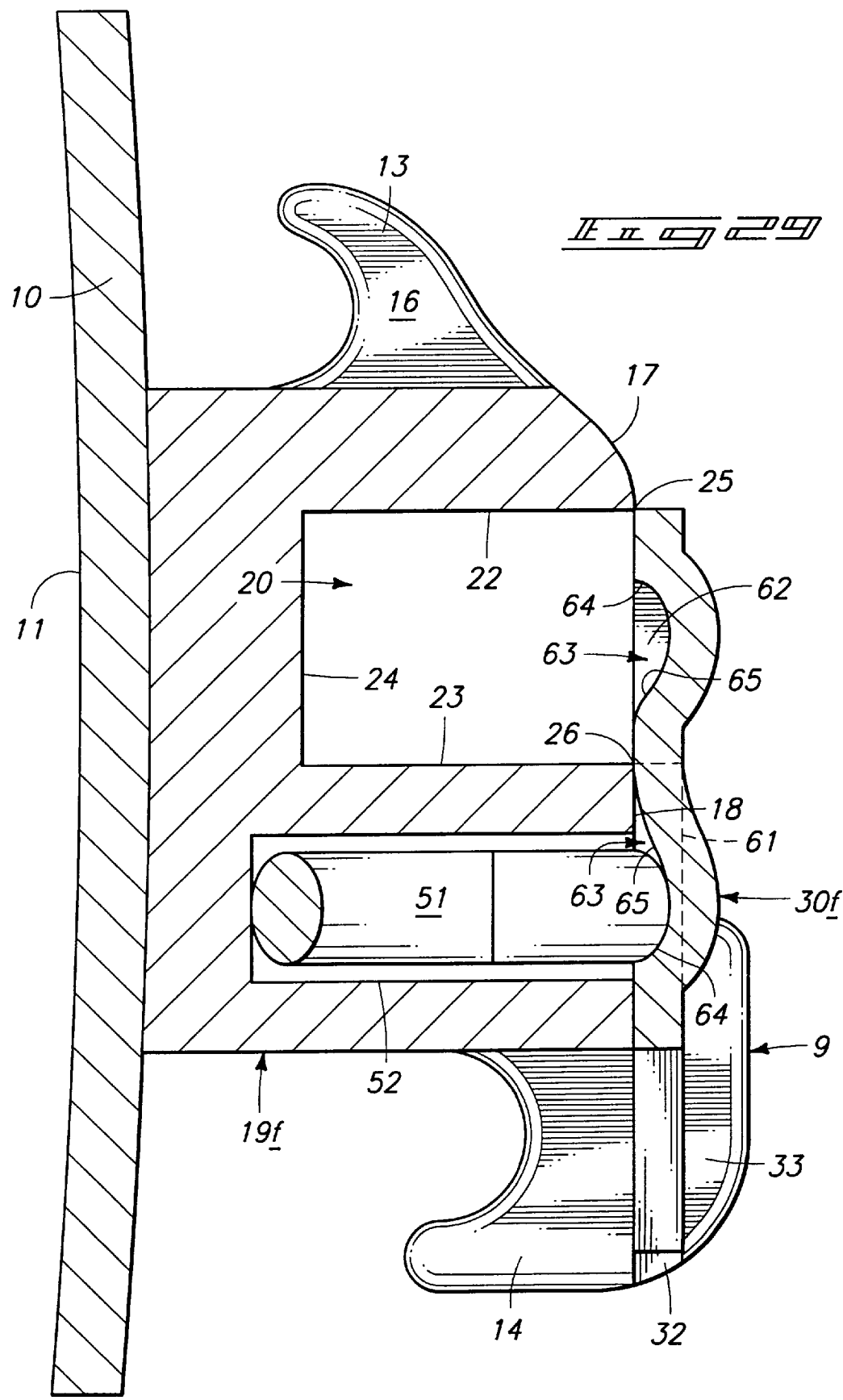
FIG. 29 is an elevational cross-section view taken along line 29—29 in FIG. 28.
Figure 30:
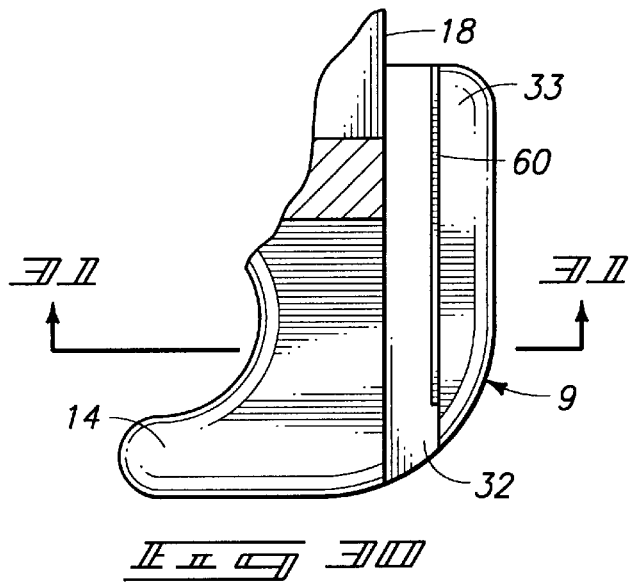
FIG. 30 is a fragmentary elevational cross-section view of the lower right corner of FIG. 29, with the slide not illustrated.
Figure 31:
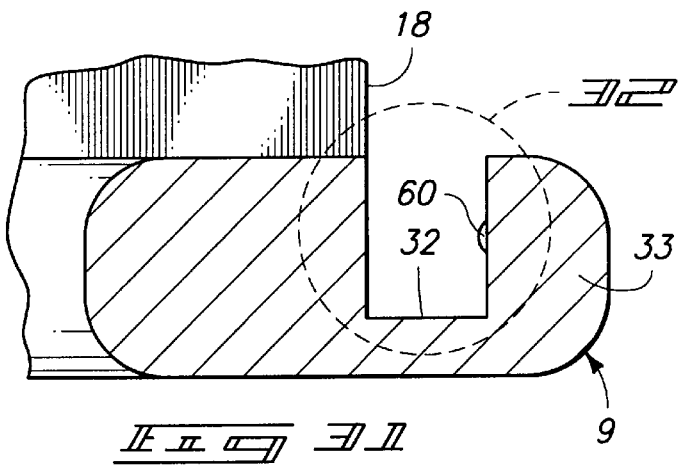
FIG. 31 is an enlarged fragmentary cross-sectional view taken along line 31—31 in FIG. 30.
Figure 32:
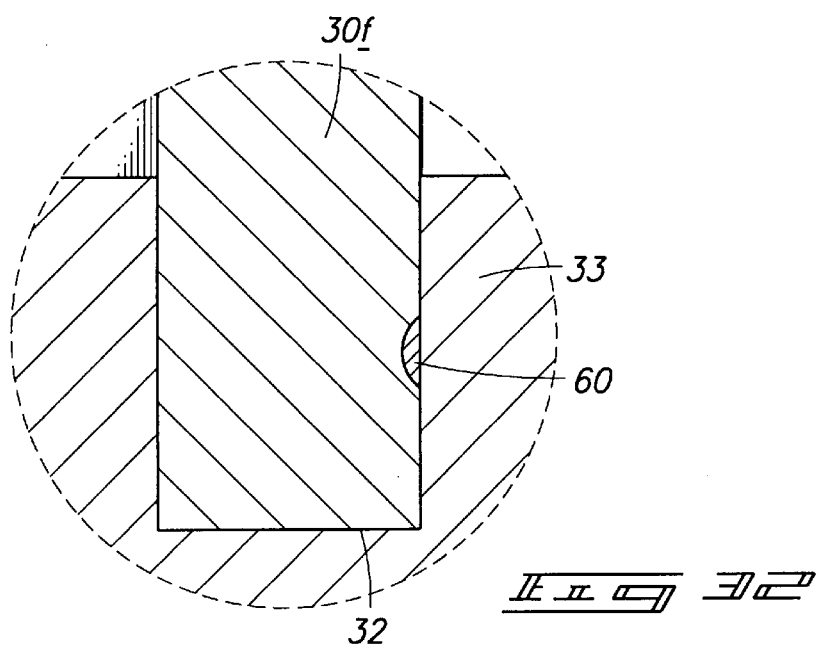
FIG. 32 is an enlarged cross-sectional view of the encircled area within FIG. 31, showing the engaged slide edges.

To achieve minimal interference with normal occlusion, the guides 9 are preferably located at a position spaced from the archwire slot 20 by forming the guides 9 over the tie wing extensions 14 (see FIG. 29). The upper end of the guide 9 shown in FIG. 29 is spaced from the corner 26 that defines the adjacent lower edge of archwire slot 20.

Because guides 9 are relatively short in this instance, a pair of vertical stabilizing walls 61 are added to the bracket structure to provide additional sliding guidance to the ligating slide. Each stabilizing wall 61 includes an upright face 62 adapted to slidably engage the side edges 31 of ligating slide 30f.

The extended stabilizing walls 61 fill the gap formed between each guide 9 and the archwire slot 20. Their inner faces 62 form smooth extensions of the base of each guiding slot formed within the adjacent guide 9. Thus, the side edges 31 of the ligating slide are engaged along a substantial portion of their length by the walls 61 and the continuing base surface within each guide slot. This prevents relative lateral movement between the ligating slide 30f and the bracket 19f.

To further control relative movement between the ligating slide 30f and the bracket 19f, the inwardly projecting walls 33 of the guides 9 have upright ridges 60 formed along their inner surfaces. The thickness of each ridge is greatly exaggerated in the drawings. It should be just sufficient to provide an interference fit between the guide 9 and the ligating slide 30f received within the guide slot.

Each ridge 60 extends parallel to the intended motion of the ligating slide 30f within the guides 9. As shown, the length of each ridge 60 terminates short of the end of the guide slot 32. This provides free clearance for initial insertion of a ligating slide 30f before contacting the protruding ends of ridges 60.

When the bracket is first assembled, the interference fit between ridges 60 and ligating slide 30f will form a minute groove along the edge areas of the anterior surfaces about ligating slide 30f. These fine grooves will be complementary to the engaged ridges 60. By varying the amount of the interference fit provided by the projecting dimension of ridges 60, one can vary the manual pressure required to move ligating slide 30f relative to the receiving bracket 19f. Of primary importance, the ridges 60 also limit facial movement of the ligating slide 30f toward or away from the main body of the supporting bracket 19f.

The combination of stabilizing walls 61 and ridges 60 assures extremely accurate control of the movement of the ligating slide 30f. This is of particular importance due to the very small dimensions of the bracket when miniaturized for modern orthodontic applications.

FIG. 29 also illustrates modification of the detent structure that is more generally described with respect to previous FIGS. 18 and 19.

The bent flat spring 51 shown in FIG. 29 is identical to that previously described. It has a curved cross-sectional shape frictionally engaged within one or the other of two recesses 63 in the ligating slide 30f. The cross-section of each recess 63 includes an outer portion 64 that substantially matches the curved cross-sectional shape of spring 51. Thus, engagement of the spring 51 against the outer portion 64 of either recess 63 substantially resists compression of the spring 51 into the bracket 19f. This provides a limit to normal motion of the ligating slide 30f relative to the bracket 19f. It prevents further movement of the ligating slide 30f when the outer portion 64 is urged against the spring 51.

The cross-section of each recess 63 further includes an inner portion 65 having a reduced slope in comparison to that of its outer portion 64. This presents less resistance to compression of the spring 51 and to movement of the ligating slide 30f when the slide is being shifted between its first and second positions.

The described shaping of recesses 63 provides tactile feedback to a clinician as the ligating slide 30f is moved relative to the supporting bracket 19f. One can feel the spring pressure exerted on the ligating slide 30f as it is moved from one position to the other, and can feel further resisting pressure to movement as the spring 51 seats within each of the recesses 63.

The ligating slide 30f as shown in FIG. 29 has a relatively thin cross-section. It must be sufficiently strong to retain its substantially planar shape, but its thickness and ridge heights across its anterior surfaces must be minimized to minimize engagement by the lip surfaces and normal occlusion within a patient's mouth.

One final operative feature of significance cannot be illustrated in the accompanying line drawings, but is most helpful to those manipulating this bracket or any other ligating bracket within the mouth of a patient. This feature involves use of color to assist in the manipulation of the moving ligating slide.

It is desirable that the ligating slide 30 be differentially colored in relation to the color of the associated bracket. The differential coloration can be achieved by using differently colored metals or other materials for the two elements of the bracket, or by applying differently colored surface treatments to one or both of the elements.

The differential coloration can either be carried out over all of the visible surfaces of each element, or can be achieved by a pattern of color, such as stripes (which would also assist in minimizing the "mirror" effect previously discussed in this disclosure.

As one specific example, the visible surfaces of the bracket might be the color silver, and the visible surfaces of the ligating slide might be the color gold.

The advantage of the differential coloration feature is directly related to the size of these elements in a production product. Orthodontic bracket assemblies and ligating slides included within them are extremely small. The very small ligating slide mounted for movement on a bracket is extremely difficult to see without magnification. By coloring the bracket and ligating slide to visibly distinguish them, one using or adjusting the bracket assembly can more readily locate the ligating slide on the bracket. This will assist in efficient manipulation of the slide to open and close it as required.

In relation to the bracket configurations shown in my previous patents, the forms of the bracket detailed herein further reduce the overall width of the bracket by at least the thickness of the previously-used connecting panels that folded over the sides of the brackets to support the guides under the archwire slots. This assists in the miniaturization of the bracket, as desired by the profession.

Furthermore, the embodiments of the invention detailed in FIGS. 1–16 and 20–23 have only two elements, as opposed to the three elements (bracket, ligating slide, and flat spring) disclosed in FIGS. 17–19 and in my prior U.S. Pat. No. 5,466,151. This reduction in elements reduces production costs for the bracket and simplifies its assembly and disassembly.

The ligating slides shown in FIGS. 1–27 can be assembled on a supporting bracket by simply sliding them into the guide slots 32. The direction of entry will vary with slide design. Where a flat spring is provided within the bracket, it must be mechanically depressed in order to facilitate entry of the ligating slide into the supporting guide slots. The ligating slide can be removed at any time by pulling it, with an excess of force, beyond its normal range of movement prescribed by design of the cooperating detent structure. When required, assembly and disassembly of the bracket can be readily accomplished while within the mouth of a patient.

Much research has been done on the cellular biology of tooth movement. It has been shown that cell differentiation of mesenchymal (undifferentiated) cells to osteoblasts and osteoclasts result from forces being applied to a tooth. Published reports have suggested that oxygen must be present for this cell differentiation to take place. Others have shown much greater tooth movement occurs as a result of the application of a low continuous force versus a higher dissipating force. A low continuous force has been demonstrated to show a much healthier cellular environment in the periodontal ligament.

The present bracket has been designed to meet future need of the orthodontic profession. Orthodontics today is moving toward the blending of high-technology wires and low friction self-ligating brackets. The net result will be greater treatment quality in less time with improved patient comfort and clinical control.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A self-ligating orthodontic bracket assembly, comprising:
    a bracket having an anterior transverse archwire slot, the archwire slot including opposing side slot surfaces leading posteriorly to a base surface within the archwire slot;
    a first exposed anterior surface formed on the bracket at one side of the archwire slot and leading to a first transverse corner where it intersects one side slot surface;
    the first anterior surface being free of any projections extending anteriorly beyond the first transverse corner so as to provide an unobstructed view of the archwire slot from its one side to provide a visual guide to a user while positioning an archwire within the archwire slot;
    a pair of guides having upright inwardly facing guide slots located anteriorly from a second anterior surface formed on the bracket at the remaining side of the archwire slot, the second anterior surface leading to a second transverse corner where it intersects a second side slot surface; and
    a ligating slide having anterior and posterior surfaces between opposed side edges, the side edges of the ligating slide being movably supported only within the respective guide slots of the guides at the remaining side of the archwire slot for alternately positioning the ligating slide (1) in a retracted first position clear of the archwire slot or (2) in a cantilevered second position projecting over the opening of the archwire slot;
    the first and second corners being parallel to one another and being located in a plane directly adjacent to the plane of the posterior surface of the ligating slide.

2. The self-ligating orthodontic bracket assembly of claim 1, wherein the first exposed anterior surface extends across the full width of the bracket.

3. The self-ligating orthodontic bracket assembly of claim 1, wherein the ligating slide is substantially planar.

4. The self-ligating orthodontic bracket assembly of claim 1, further comprising:
    a detent and a complementary recess operably engageable between the ligating slide and the bracket for fixing the position of the ligating slide relative to the bracket when the ligating slide is in its cantilevered second position.

5. The self-ligating orthodontic bracket assembly of claim 1, further comprising:
    a detent projecting from the ligating slide; and
    a complementary recess formed in the bracket for reception of the detent when the ligating slide is in its cantilevered second position.

6. The self-ligating orthodontic bracket assembly of claim 1, further comprising:
    a detent and a pair of complementary recesses operably engageable between the ligating slide and the bracket for fixing the position of the ligating slide relative to the bracket;
    the ligating slide having an open edge that is juxtaposed to the second corner along the archwire slot when the slide is in its retracted first position and is juxtaposed to the first corner along the archwire slot when the slide is in its cantilevered second position.

7. The self-ligating orthodontic bracket assembly of claim 1, further comprising:
    an integral spring detent projecting posteriorly from the ligating slide;
    the spring detent being in the form of a slotted tab partially cut from the ligating slide so as to be bendable and yieldable relative to the remainder of the ligating slide; and
    a complementary recess formed in the second anterior surface of the bracket for reception of the spring detent when the ligating slide is in its cantilevered second position.

8. The self-ligating orthodontic bracket assembly of claim 1, further comprising:
    a detent projecting anteriorly from the second anterior surface of the bracket; and
    a complementary recess formed in the ligating slide for reception of the detent when the ligating slide is in its cantilevered second position.

9. The self-ligating orthodontic bracket assembly of claim 1, further comprising:

a detent projecting from the second anterior surface of the bracket; and first and second complementary recesses formed in the ligating slide for respectively receiving the detent when the ligating slide is in its retracted first position or in its cantilevered second position.

10. The self-ligating orthodontic bracket assembly of claim 1, further comprising:

a detent projecting from the second anterior surface of the bracket;

first and second complementary recesses formed in the ligating slide for respectively receiving the detent when the ligating slide is in its retracted first position or in its cantilevered second position;

the detent comprising:

a transverse flat spring projecting from a recess formed through the second anterior surface of the bracket.

11. The self-ligating orthodontic bracket assembly of claim 1, further comprising:

a detent projecting from the second anterior surface of the bracket;

first and second complementary recesses formed in the ligating slide for respectively receiving the detent when the ligating slide is in its retracted first position or in its cantilevered second position;

the detent comprising:

a transverse flat spring projecting from a recess formed through the second anterior surface of the bracket;

the flat spring having a curved cross-sectional shape frictionally engaged within one or the other of the recesses of the ligating slide;

the cross-section of each recess including an outer portion substantially matching the curved cross-sectional shape of the spring so as to substantially resist compression of the spring and further movement of the ligating slide when urged against the spring;

the cross-section of each recess further including an inner portion having a reduced slope in comparison to that of the outer portion so as to present less resistance to compression of the spring and movement of the ligating slide when the ligating slide is being shifted between its first and second positions.

12. The self-ligating orthodontic bracket assembly of claim 1, further comprising:

a recess open to the second anterior surface of the bracket;

a detent in the form of a resilient flat spring mounted within the recess, the spring having a protruding section normally positioned beyond the second anterior surface;

the ligating slide including an indentation sized and positioned to receive the protruding section of the spring, the ligating slide being releasably maintained in one of its first or second positions by engagement of the protruding section of the spring within the indentation;

the ligating slide having an open edge that is juxtaposed to the second corner along the archwire slot when the slide is in its retracted first position and is juxtaposed to the first corner along the archwire slot when the slide is in its cantilevered second position.

13. The self-ligating orthodontic bracket assembly of claim 1, further comprising:

an integral leaf spring bent inwardly along a transverse open edge of the ligating slide.

14. The self-ligating orthodontic bracket assembly of claim 1, further comprising:

an integral leaf spring extending across the full width of the ligating slide, the leaf spring being bent inwardly along a transverse open edge of the ligating slide adjacent to the archwire slot.

15. The self-ligating orthodontic bracket assembly of claim 1, wherein the ligating slide has an open transverse edge comprising a continuous rigid area;

the open transverse edge of the ligating slide constituting a passive closure over the archwire slot when the ligating slide is in its cantilevered second position.

16. The self-ligating orthodontic bracket assembly of claim 1, wherein the ligating slide has an open transverse edge comprising a continuous leaf spring area;

the open transverse edge of the ligating slide constituting an active closure over the archwire slot when the ligating slide is in its cantilevered second position.

17. The self-ligating orthodontic bracket assembly of claim 1, wherein the ligating slide has an open transverse edge comprising alternate rigid and leaf spring areas;

the open transverse edge of the ligating slide constituting an active/passive closure over the archwire slot when the ligating slide is in its cantilevered second position.

18. The self-ligating orthodontic bracket assembly of claim 1, wherein the ligating slide is differentially colored in relation to the color of the remainder of the bracket.

19. The self-ligating orthodontic bracket assembly of claim 1, wherein the guide slots are partially formed by opposed inwardly projecting walls partially overlapping the width of the bracket.

20. The self-ligating orthodontic bracket assembly of claim 1, wherein the guide slots are partially formed by opposed inwardly projecting walls partially overlapping the width of the bracket, the walls terminating along the bracket at a location spaced from the archwire slot.

21. The self-ligating orthodontic bracket assembly of claim 1, wherein the guide slots are partially formed by opposed inwardly projecting walls partially overlapping the width of the bracket, the walls terminating along the bracket at a location spaced from the archwire slot;

the bracket assembly further comprising:

stabilizing walls extending between the guides and the archwire slot, the stabilizing walls presenting opposed faces that also extend between the walls and the second anterior surface of the bracket for slidably engaging the respective side edges on the ligating slide and limiting lateral movement of the ligating slide relative to the bracket.

22. The self-ligating orthodontic bracket assembly of claim 1, wherein the guide slots are partially formed by opposed inwardly projecting walls partially overlapping the width of the bracket, each wall having an inner surface that includes a ridge extending parallel to the intended motion of the ligating slide;

the ridges providing interference fits between the walls and the corresponding portions of the ligating slide located between the walls and the second anterior surface of the bracket.

23. The self-ligating orthodontic bracket assembly of claim 1, wherein the guide slots are partially formed by opposed inwardly projecting walls partially overlapping the width of the bracket, each wall having an inner surface that includes a ridge extending parallel to the intended motion of the ligating slide;

the ridges providing interference fits between the walls and the corresponding portions of the ligating slide located between the walls and the second anterior surface of the bracket;

each ridge terminating short of one end of the inner surface of the wall on which it is formed to facilitate entry of the ligating slide between the wall and the second anterior surface of the bracket for assembly purposes.

24. A self-ligating orthodontic bracket assembly, comprising:

twin upright tie wings positioned in transversely spaced positions, each tie wing having superior and inferior extensions directed oppositely from one another;

a transverse archwire slot formed across the tie wings, the slot including opposing side slot surfaces leading posteriorly to a base surface within the archwire slot;

a first exposed anterior surface formed on a first corresponding extension of each tie wing and leading to a first transverse corner where it intersects one side slot surface;

the first anterior surface being free of any projections extending anteriorly beyond the first transverse corner so as to provide an unobstructed view of the archwire slot from its one side to provide a visual guide to one while positioning an archwire within the archwire slot;

a second corresponding extension of each tie wing including a guide having an upright inwardly facing guide slot located anteriorly from a second anterior surface formed on the remaining side of the archwire slot, the second anterior surface leading to a second transverse corner where it intersects a second side slot surface;

a ligating slide movably supported only along the second extensions of the tie wings, the ligating slide having anterior and posterior surfaces between opposed side edges which are movably supported only within the respective guide slots of the guides at the remaining side of the archwire slot for alternately positioning the ligating slide (1) in a retracted first position clear of the archwire slot and located over the second corresponding extensions of the tie wings or (2) in a cantilevered second position projecting over the opening of the archwire slot from the second corresponding extensions of the tie wings;

the first and second corners being parallel to one another and being located in a plane directly adjacent to the plane of the posterior surface of the ligating slide.

25. The self-ligating orthodontic bracket assembly of claim 24, wherein the first extensions of the tie wings are superior to the second extensions.

26. The self-ligating orthodontic bracket assembly of claim 24, wherein the second extensions of the tie wings are superior to the first extensions.

27. The self-ligating orthodontic bracket assembly of claim 24, further comprising:

an intermediate wall section transversely joining the twin upright tie wings at one side of the archwire slot, the intermediate wall section including a surface serving as a portion of a side surface along the archwire slot.

28. The self-ligating orthodontic bracket assembly of claim 24, further comprising:

first and second wall sections transversely joining the twin upright tie wings at positions superior and inferior to the archwire slot, respectively, each of the first and second walls including a surface spaced from one another and serving as a portion of a side surface along the archwire slot.

29. The self-ligating orthodontic bracket assembly of claim 24, further comprising:

a detent and a complementary recess operably engageable between the ligating slide and the bracket for fixing the position of the ligating slide relative to the bracket when the ligating slide is in its cantilevered second position.

30. The self-ligating orthodontic bracket assembly of claim 24, further comprising:

a detent and a pair of complementary recesses operably engageable between the ligating slide and the bracket for fixing the position of the ligating slide relative to the bracket;

the ligating slide having an open edge that is juxtaposed to the second corner along the archwire slot when the slide is in its retracted first position and is juxtaposed to the first corner along the archwire slot when the slide is in its cantilevered second position.

31. The self-ligating orthodontic bracket assembly of claim 24, further comprising:

a detent projecting from the ligating slide; and a complementary recess formed in the bracket for reception of the detent when the ligating slide is in its cantilevered second position.

32. The self-ligating orthodontic bracket assembly of claim 24, further comprising:

an integral spring detent projecting inward from the ligating slide;

the spring detent being in the form of a slotted tab partially cut from the ligating slide so as to be bendable and yieldable relative to the remainder of the ligating slide; and a complementary recess formed in the second anterior surface of the bracket for reception of the detent when the ligating slide is in its cantilevered second position.

33. The self-ligating orthodontic bracket assembly of claim 24, further comprising:

a detent projecting from the second anterior surface of the bracket; and a complementary recess formed in the ligating slide for reception of the detent when the ligating slide is in its cantilevered second position.

34. The self-ligating orthodontic bracket assembly of claim 24, further comprising:

a detent projecting from the second anterior surface of the bracket; and first and second complementary recesses formed in the ligating slide for respectively receiving the detent when the ligating slide is in its retracted first position or in its cantilevered second position.

35. The self-ligating orthodontic bracket assembly of claim 24, further comprising:

a detent projecting from the second anterior surface of the bracket; and first and second complementary recesses formed in the ligating slide for respectively receiving the detent when the ligating slide is in its retracted first position or in its cantilevered second position;

the detent comprising:

a transverse flat spring projecting from a recess formed through the second anterior surface of the bracket.

36. The self-ligating orthodontic bracket assembly of claim 24, further comprising:

a detent projecting from the second anterior surface of the bracket;

first and second complementary recesses formed in the ligating slide for respectively receiving the detent when the ligating slide is in its retracted first position or in its cantilevered second position;

the detent comprising:
- a transverse flat spring projecting from a recess formed through the second anterior surface of the bracket;
- the flat spring having a curved cross-sectional shape frictionally engaged within one or the other of the recesses of the ligating slide;
- the cross-section of each recess including an outer portion substantially matching the curved cross-sectional shape of the spring so as to substantially resist compression of the spring and further movement of the ligating slide when urged against the spring;
- the cross-section of each recess further including an inner portion having a reduced slope in comparison to that of the outer portion so as to present less resistance to compression of the spring and movement of the ligating slide when the ligating slide is being shifted between its first and second positions.

37. The self-ligating orthodontic bracket assembly of claim 24, further comprising:
- a recess open to the second anterior surface of the bracket;
- a detent in the form of a resilient flat spring mounted within the recess, the spring having a protruding section normally positioned beyond the second anterior surface;
- the posterior surface of the ligating slide including an indentation sized and positioned to receive the protruding section of the spring, the ligating slide being releasably maintained in one of its first or second positions by engagement of the protruding section of the spring within the indentation.

38. The self-ligating orthodontic bracket assembly of claim 24, further comprising:
- a integral leaf spring bent inwardly along a transverse open edge of the ligating slide adjacent to the archwire slot.

39. The self-ligating orthodontic bracket assembly of claim 24, further comprising:
- an integral leaf spring extending across the full width of the ligating slide, the leaf spring being bent inwardly along a transverse open edge of the ligating slide adjacent to the archwire slot.

40. The self-ligating orthodontic bracket assembly of claim 24, wherein the ligating slide has an open transverse edge comprising a continuous rigid area;
- the open transverse edge of the ligating slide constituting a passive closure over the archwire slot when the ligating slide is in its cantilevered second position.

41. The self-ligating orthodontic bracket assembly of claim 24, wherein the ligating slide has an open transverse edge comprising a continuous leaf spring area;
- the open transverse edge of the ligating slide constituting an active closure over the archwire slot when the ligating slide is in its cantilevered second position.

42. The self-ligating orthodontic bracket assembly of claim 24, wherein the ligating slide has an open transverse edge comprising alternate rigid and leaf spring areas;
- the open transverse edge of the ligating slide constituting an active/passive closure over the archwire slot when the ligating slide is in its cantilevered second position.

43. The self-ligating orthodontic bracket assembly of claim 24, wherein the guide slots are partially formed by opposed inwardly projecting walls partially overlapping the width of the bracket.

44. The self-ligating orthodontic bracket assembly of claim 24, wherein the guide slots are partially formed by opposed inwardly projecting walls partially overlapping the width of the bracket, the walls terminating along the bracket at a location spaced from the archwire slot.

45. The self-ligating orthodontic bracket assembly of claim 24, wherein the guide slots are partially formed by opposed inwardly projecting walls partially overlapping the width of the bracket, the walls terminating along the bracket at a location spaced from the archwire slot;
- the bracket assembly further comprising:
  - stabilizing walls extending between the guides and the archwire slot, the stabilizing walls presenting opposed faces that also extend between the walls and the second anterior surface of the bracket for slidably engaging the respective side edges on the ligating slide and limiting lateral movement of the ligating slide relative to the bracket.

46. The self-ligating orthodontic bracket assembly of claim 24, wherein the guide slots are partially formed by opposed inwardly projecting walls partially overlapping the width of the bracket, each wall having an inner surface that includes a ridge extending parallel to the intended motion of the ligating slide;
- the ridges providing interference fits between the walls and the corresponding portions of the ligating slide located between the walls and the second anterior surface of the bracket.

47. The self-ligating orthodontic bracket assembly of claim 24, wherein the guide slots are partially formed by opposed inwardly projecting walls partially overlapping the width of the bracket, each wall having an inner surface that includes a ridge extending parallel to the intended motion of the ligating slide;
- the ridges providing interference fits between the walls and the corresponding portions of the ligating slide located between the walls and the second anterior surface of the bracket;
- each ridge terminating short of one end of the inner surface of the wall on which it is formed to facilitate entry of the ligating slide between the wall and the second anterior surface of the bracket for assembly purposes.

48. The self-ligating orthodontic bracket assembly of claim 24, wherein the ligating slide is differentially colored in relation to the color of the remainder of the bracket.

49. The self-ligating orthodontic bracket assembly of claim 24, wherein the exposed first anterior surface extends across the full width of the bracket.

50. The self-ligating orthodontic bracket assembly of claim 24, wherein the ligating slide is substantially planar.

51. An orthodontic bracket assembly, comprising:
- a bracket having a transverse archwire slot; and
- a ligating slide movable between (1) a first position clear of the archwire slot or (2) a second position projecting over the opening of the archwire slot;
- the ligating slide being differentially colored in relation to the color of the bracket, whereby the slide can more easily be located on the bracket.

52. A self-ligating orthodontic bracket assembly, comprising:
- a bracket having a transverse archwire slot; and
- a ligating slide movable between (1) a first position clear of the archwire slot or (2) a second position projecting over the opening of the archwire slot;
- the ligating slide having an open transverse edge comprising alternate rigid and leaf spring areas;

the open transverse edge of the ligating slide constituting an active/passive closure over the archwire slot when the ligating slide is in its cantilevered second position.

53. An active/passive ligating slide for use in a self-ligating orthodontic bracket assembly including a bracket having a transverse archwire slot; the ligating slide comprising:

spaced side edges adapted to be guided along a bracket having a transverse archwire slot wherein the ligating slide is selectively movable between (1) a first position clear of the archwire slot or (2) a second position projecting over the opening of the archwire slot, an open transverse edge having alternate rigid and leaf spring areas;

the open transverse edge of the ligating slide constituting an active/passive closure over the archwire slot when the ligating slide is in its cantilevered second position.

\* \* \* \* \*